(12) United States Patent
Powell et al.

(10) Patent No.: US 6,813,568 B2
(45) Date of Patent: Nov. 2, 2004

(54) SYSTEM AND PROCESS FOR MICROFLUIDICS-BASED AUTOMATED CHEMISTRY

(75) Inventors: Michael Powell, Boston, MA (US); Paul Tempst, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 10/203,235

(22) PCT Filed: Jan. 9, 2002

(86) PCT No.: PCT/US02/00370

§ 371 (c)(1),
(2), (4) Date: Dec. 11, 2002

(87) PCT Pub. No.: WO02/055188

PCT Pub. Date: Jul. 18, 2002

(65) Prior Publication Data

US 2003/0158674 A1 Aug. 21, 2003

(51) Int. Cl.[7] .................... G06F 19/00; G01N 31/00; G01N 1/10
(52) U.S. Cl. .................. 702/31; 73/864.84; 422/99; 435/286.5
(58) Field of Search ................. 702/31; 73/864.83, 73/864.84, 61.52; 418/63; 422/63, 64, 65, 67, 99, 100; 435/6, 91.2, 287.1, 286.5, 289.1; 356/73

(56) References Cited

U.S. PATENT DOCUMENTS

| | | | | |
|---|---|---|---|---|
| 3,961,534 A | * | 6/1976 | Gundelfinger | 73/864.84 |
| 4,068,528 A | * | 1/1978 | Gundelfinger | 73/864.84 |
| 4,427,351 A | * | 1/1984 | Sano | 418/63 |
| 4,674,323 A | * | 6/1987 | Rulf et al. | 73/61.52 |
| 5,273,905 A | * | 12/1993 | Muller et al. | 435/286.5 |
| 6,415,670 B1 | * | 7/2002 | Ohkura et al. | 73/864.83 |
| 6,427,731 B1 | * | 8/2002 | Horn | 141/67 |
| 2003/0156989 A1 | * | 8/2003 | Safir et al. | 422/99 |

* cited by examiner

Primary Examiner—John Barlow
Assistant Examiner—John Le
(74) Attorney, Agent, or Firm—Klauber & Jackson

(57) ABSTRACT

A system for carrying out reactions that includes a small volume rotary selector valve having a plurality of peripheral ports and a small volume rotary switching valve, also having a plurality of peripheral ports, where the selector valve and switching valve are controlled by a computer. The rotary selector valve is connected by common port to a peripheral port of the rotary switching valve. The internal volumes of the rotary selector valve and rotary switching valves are 1.5 µl or less.

11 Claims, 17 Drawing Sheets

FIG. 1C

EXAMPLES OF REAGENTS

| | |
|---|---|
| 11 | 1% PHENYL ISOTHIOCYANATE IN HEPTANE |
| 12 | 12.5% TRIMETHYLAMINE IN WATER |
| 13 | TRIFLUOROACETIC ACID |
| 14 | 25% TRIFLUOROACETIC ACID IN WATER |
| 15 | PTH AMINO ACID STANDARD |
| 16 | NORLEUCINE STANDARD |

EXAMPLES OF WASH SOLVENTS

| | |
|---|---|
| 141 | HEPTANE |
| 142 | ETHYL ACETATE |
| 143 | BUTYL CHLORIDE |
| 144 | 10% ACETONITRILE IN WATER |
| 221 | WATER WITH TETRAHYDROFURAN |
| 222 | ACETONITRILE |

EXAMPLES OF GAS SOURCES

| | |
|---|---|
| 174a | 2.0 PSI ARGON |
| 174b | 2.0 PSI ARGON |
| 174c | 4.0 PSI ARGON |
| 174d | 12.0 PSI ARGON |
| 174e | 24.0 PSI ARGON |
| 174f | 50.0 PSI ARGON |

FIG. 8
A
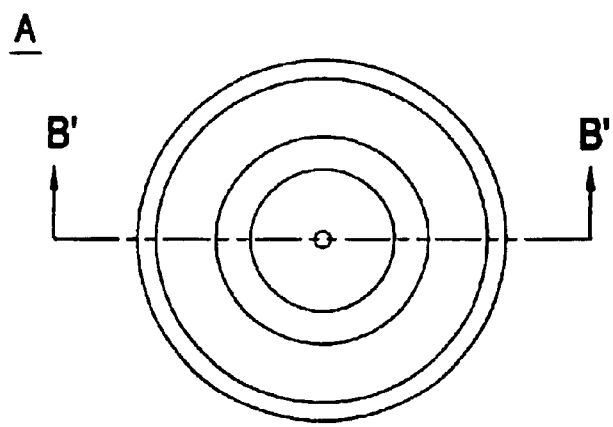
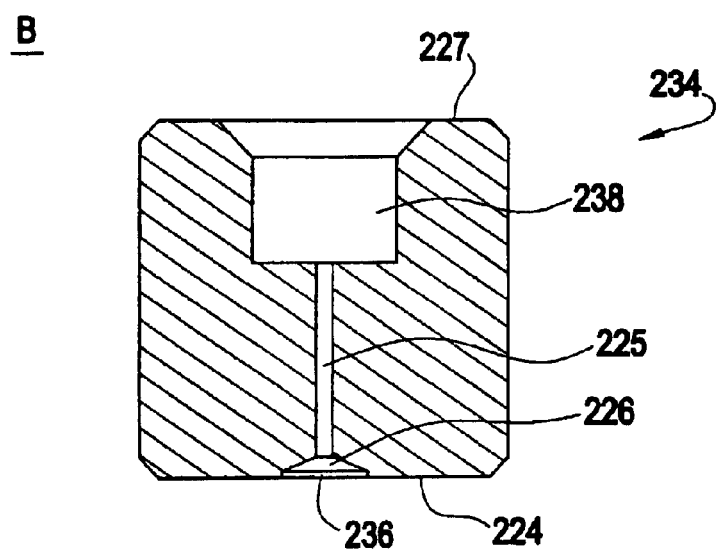
C
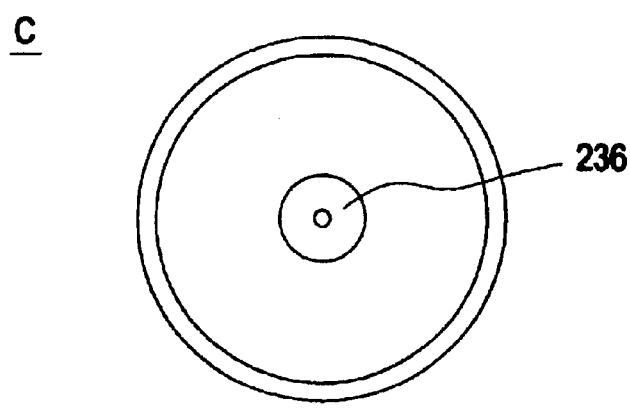

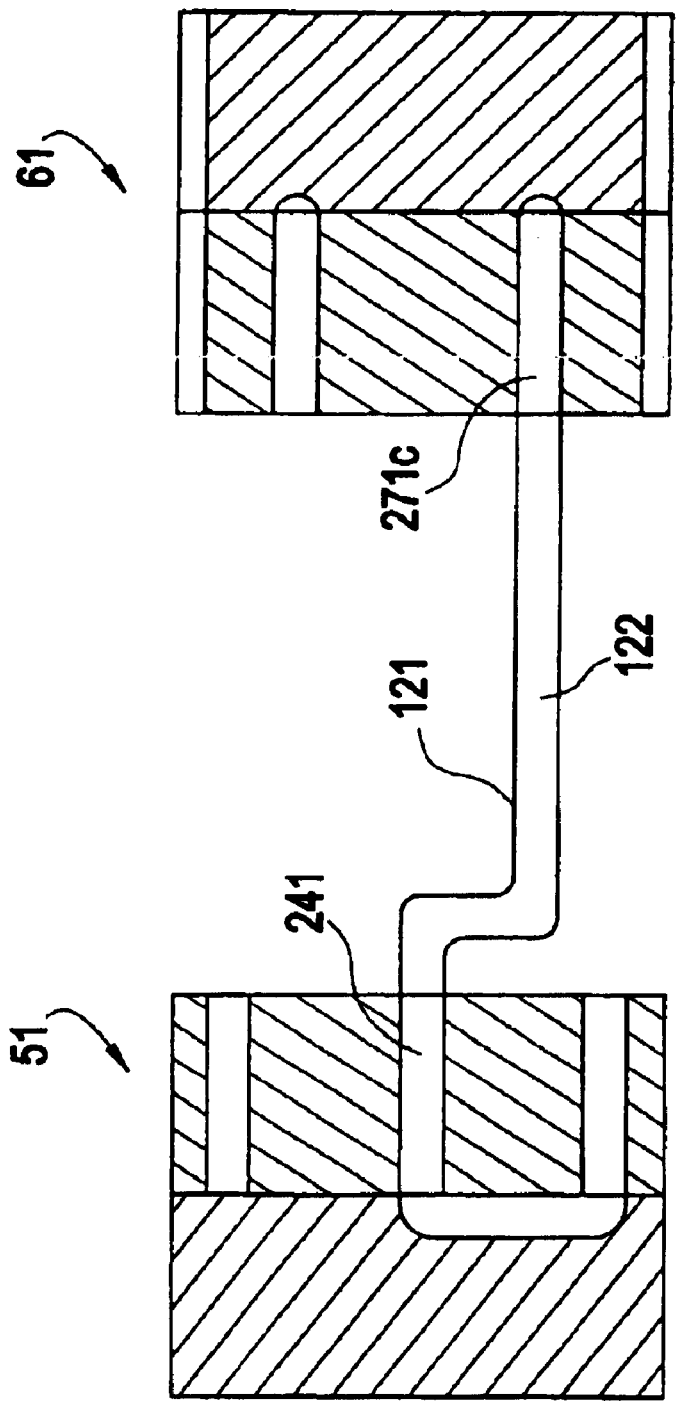

SYSTEM AND PROCESS FOR MICROFLUIDICS-BASED AUTOMATED CHEMISTRY

This application claims priority from PCT/US02/00370 field on Jan. 9, 2002.

The research leading to the present invention was supported, at least in part, by NSF grant DBI-942012 and Development Funds from NCI Grant P30 CA08748. Accordingly, the Government may have certain rights in the invention.

BACKGROUND

This invention relates to the field of microfluidics-based automated chemistry.

Many analytical chemical problems involve the analysis of small amounts of a sample. The ability to do chemical reactions in small volumes of liquid is important in such cases as the reaction rate can decrease to commercially unacceptable levels if the concentration of the sample is too low. Additionally, for analytical devices used to monitor the results of such reactions, it is frequently important that the reaction product be in a small volume in order that a detectable concentration be present. The present invention offers a solution to the problem of doing chemical reactions in small volumes, to doing a succession of such reactions, and to doing them on an automated basis.

Although the present invention will be seen to have general chemical applicability, its application to biomedical research is of particular interest. Post-genome research will likely focus on understanding the cellular chemistry, circuitry and communications underlying life's vital processes. Biomedical scientists, for instance, will aim to identify how genetic determinants of disease alter cellular physiology and response to agonists. Predictably, all this will involve biochemical analysis of larger numbers of samples containing ever lower concentrations of analyte. In most cases, analyses entail multistep procedures, including chemical and enzymatic reactions. Not only will automation prove essential in such cases, it must also be done in fully integrated instruments that incorporate the smallest possible reaction vessels and wetted surfaces. Progress towards this goal has come from nano-fabricated devices[1-4] ("lab-on-a-chip"), but severe limitations on sample volume may restrict the technology to fast, parallel analysis of abundant and/or amplifiable (e.g. by PCR) molecules. What's needed is automation whereby trace analytes are processed in their entirety. We wanted to construct such a device, initially using chemical protein sequencing as a model system. Such chemistries have been replaced during recent years by mass spectrometry as a means to protein identification.[5-8] Yet, the fact remains that chemical analysis can yield rather long stretches of easy to interpret sequence, including on intact proteins, with the caveat that current instruments are at least ten to twenty times less sensitive than most mass analyzers.

Traditionally, protein chemical sequencing is done by stepwise removal of amino acids from the N-teminal end, one at a time. In this method, the Edman degradation,[9,10] phenyl isotliocyanate (PITC) is coupled to the alpha-amino group of the polypeptide to form a phenyl thiocarbamyl (PTC)-derivative; anhydrous acid causes selective release of the PTC-amino, leaving a truncated peptide chain. The resulting anilino thiazolinone amino acid (ATZ-aa) is converted with aqueous acid to a more stable phenyl thiohydantoin amino acid (PTH-aa) and identified. The latter step cannot be done in the presence of polypeptide as it would cause hydrolysis; thus, the ATZ-aa must be extracted. The procedure was partially automated, first by Edman in the 'spinning cup' version,[11] and later in Laursen's solid-phase sequencer.[12] Conversion was initially done outside the machine, but later incorporated into the automated process by Wittman-Liebold.[13] Until then, thin layer or gas chromatography were used for PTH-aa identification; Hunkapiller and Hood were among the first to routinely use reversed-phase high performance liquid chromatography (RP-HPLC) for this purpose.[14] Around 1980, the gas-phase (GP) sequencer was developed by Hewick and coworkers.[15] Here, wash-out of the peptide from the reaction vessel was prevented by non-covalent immobilization on a glass-fibre disc and by delivering polar liquids as vapors. The process has been further automated by coupling HPLC identification of PTH-aa's 'on-line' with the sequencer; contents of the conversion flask are hereby directly transferred into the LC injector loop. Since then, progress has come from incremental improvements such as femtomole level HPLC detection,[16] rigorous instrument optimization and maintenance routines,[17] and the use of a smaller reaction cartridges.[17-19] Combined with improved micro-preparation of polypeptides,[20-22] chemical sequencing at the 1–3 picomole level is currently possible and extended sequencing runs with femtomole level signal have been reported.[16,23,24] Additional modifications to the process have since been suggested that should allow true femtomole level sequencing. All relate to increased sensitivities of amino acid derivative detection. This can be accomplished by miniaturizing the HPLC-based PTH-aa detection system, or by producing modified Edman end-products of higher detect ability, or both.

Whereas femtomole level PTH-aa separations on microbore columns can be done,[19,25] the use of capillary columns (300-micron ID) is more problematic, as injection volumes of over 0.5 $\mu$L cause baseline disturbances.[26] Complete injection (or even 10%) of the sample in a 0.5-$\mu$L volume is not possible from any commercial automated sequencer. This also applies to capillary zone electrophoresis (CZE)-based amino acid-derivative detection systems.[27]

Considerable effort has been expended to generate fluorescent amino acid derivatives as end-products of Edman chemistry. Fluorescent sequencing is especially appealing since the introduction of sub-attomole amino acid analysis by CZE with laser-induced fluorescence.[27,28] Yet, again, loading volumes are in the nanoliter range, several orders of magnitude less than what is typically present in a sequencer flask. Another approach to 'high-detect ability' is the generation of quaternary or tertiary amine thiohydantoin amino acid derivatives, analyzable by mass spectrometry at the low femtomole level.[29,30] However, both methods never progressed beyond the R&D stage.

Development of any Edman based, femtomole-level technique requires satisfying two major criteria: (i) quantitative transfer, in the smallest possible volume, of amino acid derivatives to the site of analysis; and (ii) reducing chemical background that will impede any ultra-sensitive analytical technique. This can only be accomplished by further miniaturization of the chemistry.

We describe a microfluidics-based instrument, consisting of multiple rotary valves, capillary tubing and miniaturized reaction vessels, for the purpose of performing automated chemical and biochemical reactions on a very small scale. Close to 100% of the reaction end-products are available in a minimal volume ($\leq 5$ $\mu$L) inside a pressurized mirco-vial for subsequent analysis. This makes the system compatible with capillary HPLC and, in principle, with continuous flow nano-electrospray mass spectrometry. Total control of flow path combinations and directions, temperatures and gas pressures enables precise execution of complex biochemical laboratory procedures. Instrument performance was convincingly demonstrated by partially sequencing 100 femtomoles of an intact protein using classical Edman chemistry in combination with capillary-bore liquid chromatography. To our knowledge, this is the smallest amount of protein ever reported to be successfully analyzed in this way.

SUMMARY OF THE INVENTION

The invention is a chemical system and related processes that utilize small-volume rotary selector valves and small-volume rotary switching valves in combination under the control of a computer. The small rotary valves are particular well-suited to computer control. As a result, a single system can be programmed to do a variety of tasks by changing the program but leaving the system's components substantially intact.

As a result, in a general aspect the invention is a system for carrying out one or more chemical reactions, said system comprising a rotary selector valve and a rotary switching valve, each valve under the control of a computer, the internal volumes of the selector and switching valves each being 1.5 µl or less.

Specific aspects of the invention that are of particular interest are the selector valve-switching valve combination, a core system for regulating a sequence of reactions, a core system adapted for polymer sequence analysis, and processes that implement the systems. The core systems can, as indicated by the use of the word "comprising" in their description, be either used as stand-alone systems or be part of larger systems.

Selector Valve-Switching Valve Combination

An important aspect of the invention is a rotary valve combination comprising a rotary selector valve (with its plurality of peripheral ports) connected by its central common port to a peripheral port of a rotary switching valve. The connection is preferably accomplished by a conduit means (e.g., a tube or capillary). It is preferred that the conduit means have an internal volume between 0.5 µL and 10 µL.

The Rotary Selector Valves

It is preferred that the rotary selector valve comprise, in a first unit (e.g., the stator), a central common port and a circular array of a plurality of peripheral ports such that the main axis of the common port is the same is as the main axis through the circular array, and wherein said valve comprises, on a second unit, a radial connector channel, the first and second units being juxtaposed such that there is a single continuous selector channel formed by the common port, the connector channel, and a peripheral port, the selection of the peripheral port under control of the computer (the control preferentially effectuated by rotating the second unit), the internal volume of the continuous selector channel being the internal volume of the valve, Preferably the two units are positioned in flat contact with each other, the flat contacting surface of the first unit against the flat contacting surface of the second unit. Contact between the two units is such that both the common port and a peripheral port meet the connector channel. This is optimally done by constructing the connector channel as a groove on the contacting surface of the second unit. It is preferred, but not required, that the common port act as an output port and that the connected peripheral port act as an input port, but the reverse relationship between the ports is also possible. The total internal volume (central port plus connector channel plus peripheral port) is preferably 1.5 µL or less (more preferably in the range 0.04 µL to 1.5 µL, most preferably 0.1 µL to 0.5 µL).

The Rotary Switching Valves

It is preferred that the rotary switching valve comprise a circular array of three or more peripheral ports in a first unit (e.g., the stator) and a connector channel in a second unit, the two units being juxtaposed such that there is a continuous switching channel formed by a first peripheral port, the connector channel, and a second peripheral port, the selection of two peripheral ports being under the control of the computer (the control preferentially effectuated by rotating the second unit), the internal volume of the continuous switching channel being the internal volume of the valve.

Preferably the two units are positioned in flat contact with each other, the flat contacting surface of the first unit against the flat contacting surface of the second unit. Contact between the two units is such that two peripheral ports meet the connector channel. This is optimally done by constructing the connector channel as a groove on the contacting surface of the second unit. (The groove can be straight or curved). The total internal volume (central port plus connector channel plus peripheral port) is preferably 1.5 µL or less (more preferably, in the range 0.04 µL to 1.5 µL, most preferably 0.1 µL to 0.5 µL).

System For Regulating a Sequence of Reactions

In a general aspect the invention is a computerized system for regulating complex reaction sequences in small volumes of solution, said system comprising:

a reaction vessel (for holding a volume of fluid in which a reaction takes place);

a first and second reagent vessel (for holding fluid reagents), said vessels each connected to a gas source, a rotary valve combination connected to receive fluid from said reagent vessels and to deliver fluid to said reaction vessel, said combination optionally with other receiving-delivery capabilities, said rotary valve combination comprising a multi-position rotary selector valve connected to a rotary switching valve;

a computer connected to said valve combination so that said computer controls both whether the switching valve is configured to allow or to not allow fluid flow to the reaction vessel and whether the selector valve is configured for input from the first or second reagent vessel; and wherein the internal volume of each of said valves along the path of fluid flow, is 1.5 µL or less, (preferably in the range 0.04 µL to 1.5 µL, more preferably 0.1 µL to 0.5 µL).

Each gas source is selected from a group of one or more gas sources each comprising a gas under pressure, said gas optionally differing from source to source. Any gas or gas combination that is not chemically reactive with a fluid or other reagent in the system can be used.

System Adapted for Polymer Sequence Analysis

In another aspect, the selector valve of the above-noted system is a first selector valve and the switching valve thereof is a first switching valve, and the system further comprises:

a second rotary selector valve connected to a second rotary switching valve;

a third rotary switching valve;

a conversion vessel connected to receive output from said third rotary switching valve, a restraining means for restraining unprocessed polymer in the reaction vessel;

third and fourth reagent vessels connected to provide fluid to said conversion vessel;

wherein said second rotary valve, second switching valve, and third switching valve are each under the control of the computer and each have an internal volume of 1.5 µl or less (preferably 0.04 µL to 1.5 µL, more preferably 0.1 µL to 0.5 µL).

In particular embodiments, the system further comprises one or more of the following:

one or more wash solution vessels (each for holding a volume of fluid, preferably a wash solution), each said vessel connected to a gas source, each said vessel providing optional input (directly or via other elements of the system) via a selector valve to the reaction vessel and/or conversion vessel; and a switching valve, under the control of the computer, for controlling fluid flow to an analytical device (such as an HPLC column or electrospray ionization mass spectrometer) from the conversion flask.

Reaction Vessel and Conversion Vessel

It is preferred that, when the first and second fluid reagents are in the reaction vessel, the volume of fluid in the reaction vessel is in the range of 0.5 $\mu$L to 10 $\mu$L (preferably 1 $\mu$L to 5 $\mu$L).

It is preferred that a volume of fluid in the conversion vessel be in the range 1 $\mu$L to 150 $\mu$L (preferably 3 $\mu$L to 50 $\mu$L, most preferably 3 $\mu$L to 15 $\mu$L).

Selector Valve Cascade

An aspect of the invention is a rotary selector valve cascade in which a plurality of peripheral ports of a first selector valve are each connected to the central common port of one of plurality of rotary selector valves that each comprise a plurality of peripheral ports, the total internal volume of each valve being 1.5 $\mu$L or less (more preferably in the range of 0.4 $\mu$L to 1.5 $\mu$L, most preferably 0.1 $\mu$L to 0.5 $\mu$L).

Process Aspect of the Invention

In another general aspect, the invention is a reaction process under the control of a computer said process comprising the steps of:

1) Delivering, from a reagent vessel under pressure from a gas source, a volume of a reagent via a delivery line to a reaction vessel wherein the total volume delivered for purposes of a reaction in the reaction vessel is in the range 0.5 $\mu$L to 10 $\mu$L, preferably 1 $\mu$L to 5 $\mu$L, and wherein flow through the delivery line is under the control of a computer-controlled rotary valve combination; Preferred is the process with an additional steps (2) and (3):

2) Washing said valve combination and delivery line with a wash-solvent; and

3) Repeating step (1) optionally with a reagent, reagent vessel and/or gas source different from that used in step (1).

Process Aspect of the Invention Used to Sequence Polymers

In an aspect of the invention adapted for sequencing a polymer, the process comprises the steps of:

(1) Placing a polymer (preferably in the range 5 to 500 femtomoles, more preferably 20 to 250 femtomoles, most preferably 50 to 200 femtomoles) in a reaction vessel, said polymer restrained in said vessel, the restraining preferably accomplished by adsorption of the polymer to a solid support;

(2) Delivering to said reaction vessel, from a first reagent vessel under pressure from a gas source, a volume of a first fluid, said fluid comprising a first reagent, which reagent will react with a terminal monomer on the polymer;

(3) Delivering to said reaction vessel, from a second reagent vessel under pressure from a gas source, a volume of a second fluid, which fluid (the fluid can be a solvent or a solution of a solute in a solvent) will cause a terminal monomer-reagent moiety to be cleaved from the polymer;

(4) causing all or part of the fluid in the reaction flask to be transferred under gas pressure via a delivery line to a conversion flask while allowing the polymer, less the terminal monomer, to remain in the reaction vessel;

(5) Prior or after step (4), delivering from a third reagent vessel under pressure from a gas source a volume of a third fluid such that the combination of said fluid and the fluid transferred in step (4) to the reaction flask will cause the terminal monomer-reagent moiety to be cleaved to create a terminal monomer free of covalently bound reagent;

(6) Transferring under gas pressure from a gas source said terminal monomer created in step (5) to an analytical device that will identify the nature of the terminal monomer.

It is preferred that each volume delivered in steps (2), (3), (4), (5), is in the range 0.2 $\mu$L to 10 $\mu$L, (preferably 0.5 $\mu$L to 5 $\mu$L). Independently, it is preferred that the volume delivered in step (6) is in the range 1 $\mu$L to 10 $\mu$L, (preferably 2 $\mu$L to 5 $\mu$L).

In a preferred embodiment of the process adapted for sequencing a polymer, the process comprising steps (1)–(6), is performed a plurality of times.

Air-Free Reaction System

In preferred embodiments of the processes, the reaction vessel and the conversion vessel are kept free of air and oxygen. The ability to do this effectively is an advantage of the present invention.

Sequential Treatment with Acid and Base

In particular embodiments of the processes, the process comprises sequentially delivering acid, organic solvent, and base to the reaction vessel. The ability to do this effectively is an advantage of the present invention.

Applications of the Invention

Examples of such applications are:

1) automated reactor for solution chemistry;

2) automated reactor for liquid "flow-through" chemistry;

3) automated reactor for gas-phase chemistry;

4) automated sample preparation, modification, and reaction prior to electrospray ionization mass spectrometry;

5) automated enzymatic digestion of proteins, nucleic acids and complex carbohydrates;

6) thermostatic control for sample preparation, modification and reaction (including the above uses);

7) automatic precision volume metering utilizing loops with volume range 0.1 microliter and above;

8) automated selection of samples for any use described above.

Specific Polymer Applications

In one set of embodiments, the system is adopted for processing a polymer in step with fashion, one monomer at a time.

Example of such processing are:

1) the determination of the amino acid sequence of a polypeptide;

2) the determination of the base sequence of a nucleic acid; and 3) the determination of the sugar sequence of a polysaccharide;

BRIEF DESCRIPTION OF THE DRAWINGS

FIG. 8. Bottom block of reaction vessel. A. A bottom planar view. B. A sectional drawing along the line B'—B' in A. C. A top planar view.

FIG. 11. Schematic partially sectional view drawing of a selected portion of a rotary valve combination in which a valve (FIG. 6) is connected via a capillary to a selector valve (FIG. 5).

DETAILED DESCRIPTION OF THE INVENTION

Abbreviations and Glossary

ATZ-aa stands for anilino thiazolinone amino acid.
BLG stands for beta-lactoglobulin.
BuCl stands for butyl chloride.
CLC stands for capillary liquid chromatography
A computer is an electronic device that receives input information in electronic for and process that information electonically or electromagnetically to create electronic output signals that can be converted to printed material, converted electronically displayed material, or otherwise further processed. Typical computers are personal computers such as made by IBM or other comapnies but both more sophisticated computers can also be used and, conversely, the computer can be one of much simpler construction than a personal computer by virtue of the fact that it is dedicated to the process and systems of the invention.

CZE stands for capillary zone electrophoresis.
DMPTU stands for dimethylphenylthiourea.
DPTU stands for diphenylthiourea
EtAc stands for ethyl acetate.
GP stands for gas-phase.
HPLC stands for high performance liquid chromatography.
LC stands for liquid chromatography.
Lys stands for lysine.
10% MeCN and 10% MeCN/$H_2O$ stands for 10% acetonitrile in water.
MS/MS stands for tandem mass spectrometry.
ESI stands for electrospray ionization.
PCR stands for polymeric chain reaction.
PITC stands for phenyl isothiocyanate.
Plurality means 2 or more.
PSMSK stands for the automated micro-fluidics system 100.
PTC stands for phenyl thiocarbamyl.
PTH-aa stands for phenyl thiohydantoin amino acid.
Reagents include any fluids or solids that participate in chemical reactions and also any solution or solution components in which said fluids or solids are dissolved or suspended.
RP-HPLC stands for reversed-phase high performance liquid chromatography
25% TFA and 25% TFA/$H_2O$ stands for 25% TFA (v/v) in $H_2O$
0.1% TFA stands for 0.1% TFA in $H_2O$
TFA stands for trifluoroacetic acid.
THF stands for tetrahydrofuran.
TMA stands for trimethylamine.
The terms "path of fluid flow" and "flow through channel" are used interchangeably. For a particular component of the system in a given configuration (e.g., a particular valve setting), the terms reprsent the total path followed by fluid within that component in that configuration.
"Under pressure" means under greater than atmospheric pressure.
Val stands for valine.
A "volumetric loop" is a conduit that can be either straight, looped, helical, or otherwise curved. "Loop" here is a term of art.
"Wash solutions", also referred to as "wash solvents", are solutions that are used to wash a vessel or a vessel-to-vessel connector after it has been vacated by a reagent.

Overview of the Invention in Relation to the Figures

The following, by relating the invention to the Figures, is intended to exemplify the invention, not limit it.

Figure 1A:
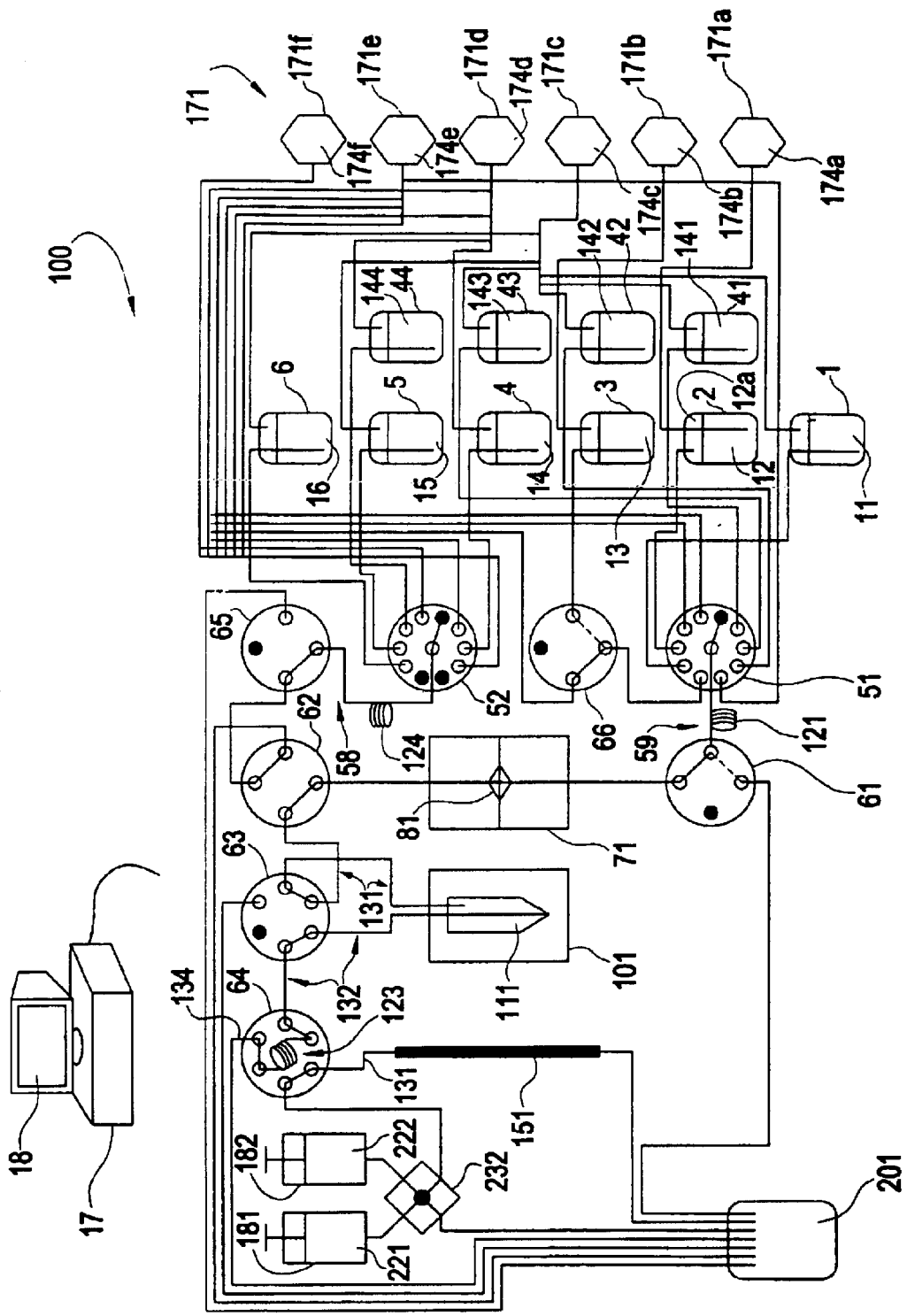
FIG. 1.(A) Schematic diagram of the 'PSMSK' automated microfluidics system. The instrument 100 is shown here in a protein sequencer configuration. Connections of the computer 17 to the other components of the system are not shown but are described in the text. (B) Legend to selected symbols seen in (A). (C) Examples of materials used with system shown in (A).

FIG. 1A shows a computerized system 100 for regulating complex reaction sequences in small volumes of solution. The system contains a reaction vessel 71 for holding a volume of fluid 81 and reagent vessels 1–6 (for holding fluid reagents 11–16, respectively)., The vessels 1–6 are each connected to a gas source, selected from a group 171. Gas sources 171a–f each contain a gas 174a–f under pressure. The system also has a rotary valve combination 59 connected to receive fluid from reagent vessels 1–2 and to deliver fluid to the reaction vessel 71. The combination can be seen to have other receiving-delivery capabilities. The rotary valve combination 59 comprises a multi-position rotary selector valve 51 connected via a conduit means 121 to a rotary switching valve 61. A computer 17 is connected to the valve combination 59 (Computer connections are described in the text herein but are not shown in the Figures.) The computer controls both whether the switching valve 61 is configured to allow or to not allow fluid flow to the reaction vessel 71 and whether the selector valve 51 is configured for input from reagent vessel 1 or from reagent vessel 2.

The system is adapted for polymer sequence analysis. To that purpose it includes a conversion vessel 101 for holding a volume of fluid 111. It also includes a restraining means 191 for restraining the unprocessed portion of the polymer in the reaction vessel 71 (See FIG. 7). The restraining means can, as in the example below, provide a surface to which the polymer can noncovalently adsorb, or it can be a component to which the polymer, e.g., via an end group, can be covalently linked. The system also has a rotary switching valve 62, under the control of computer 17, for controlling fluid flow to the conversion vessel 101 from the reaction vessel 71. The system also has a second rotary valve combination 58 connected to receive fluid from reagent vessels 4–5 and to deliver fluid to flow to said valve 62. The combination can be seen to have other receiving-delivery capabilities. The rotary valve combination 58 comprises a multi-position rotary selector valve 52 connected to a rotary switching valve 65. The computer 17 is connected via a conduit means 121 to valve combination 58 so that said computer controls both whether the switching valve 65 is configured to allow or to not allow fluid flow and whether the selector valve 52 is configured for input from reagent vessel 4 or from reagent vessel 5.

The system has additional components. It has wash solution vessels 41–44 (for holding wash solutions 141–144), the vessels connected to a gas sourceselected from group 171. Vessels 41–43 are connected as optional input to valve combination 59. Vessel 44 is optional input to valve combination 58. Additionally, the system has an analytical device 151, an HPLC Column in combination with a UV monitoring device. Other features of interest are a switching valve 64 under the control of computer 17, for controlling fluid flow to the HPLC column from the conversion flask 101. Reagent vessels 221 and 222 are sources of reagents 181 and 182 for the HPLC column. Waste vessels201 collects waste fluid.

Figure 5:
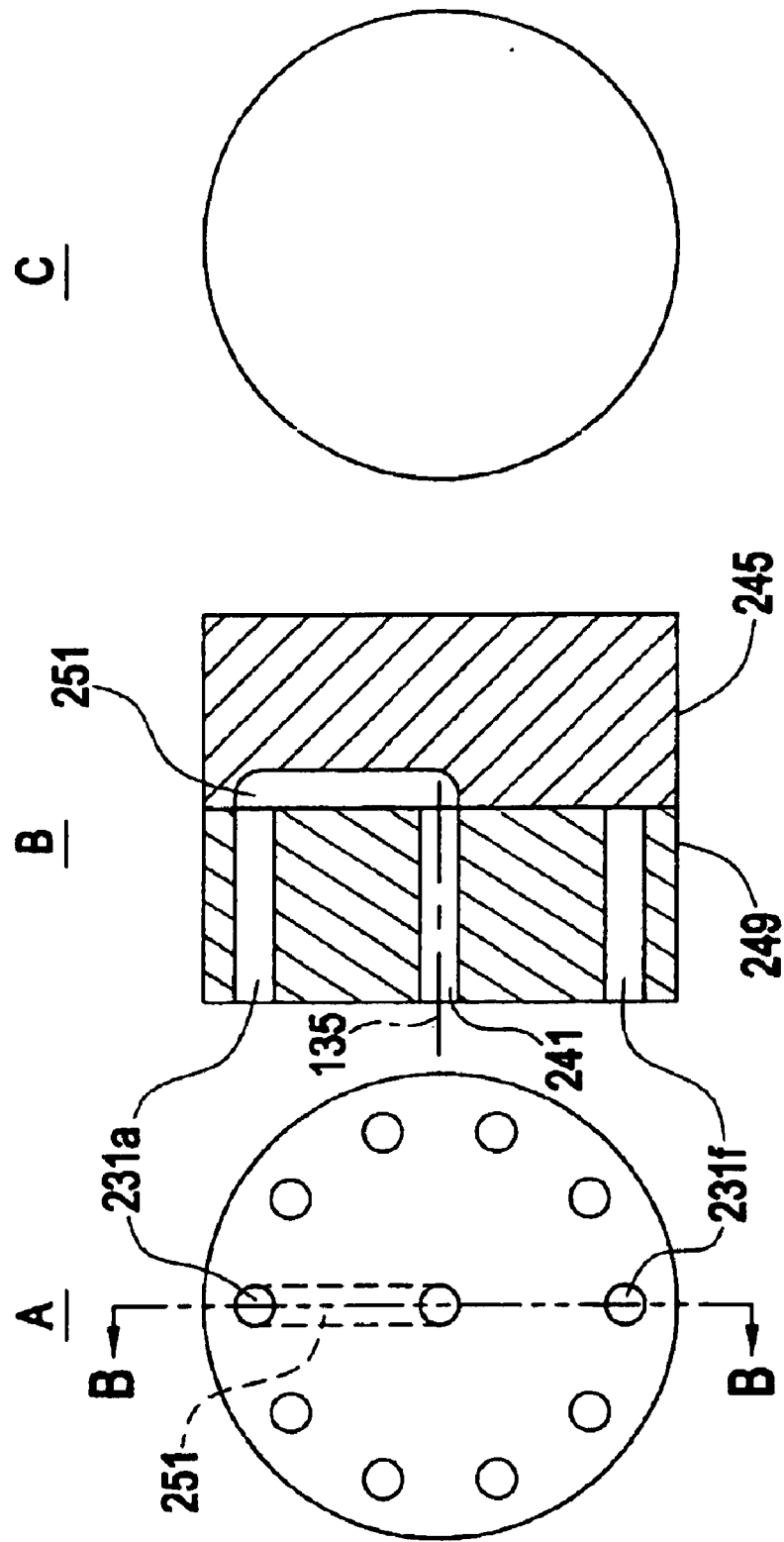
FIG. 5. Schematic drawing of selected portions of a selector valve. A. A first side planar view. B. A sectional view. C. A second side planar view.

Multiposition rotary selector valve 51 is schematically shown in FIG. 5 and, in the first unit 249 of the valve, comprises a central common port 241 and a circular array of a plurality of peripheral ports 231a–j, (only 231a and 231f are marked in FIG. 5) such that the main axis (imaginary line 135) of the central common port is the same as the main axis through the circular array. The valve also comprises, on a second valve unit 245, a radial connector channel 251 in a second unit 245 of the valve. A continuous selector channel is created by the common port 241 plus the conduit means 251 plus the peripheral port 231a. The common port 241 can be commented to any peripheral 231a–j port selected by rotation of the second unit as determined by the computer 17.

Figure 6:
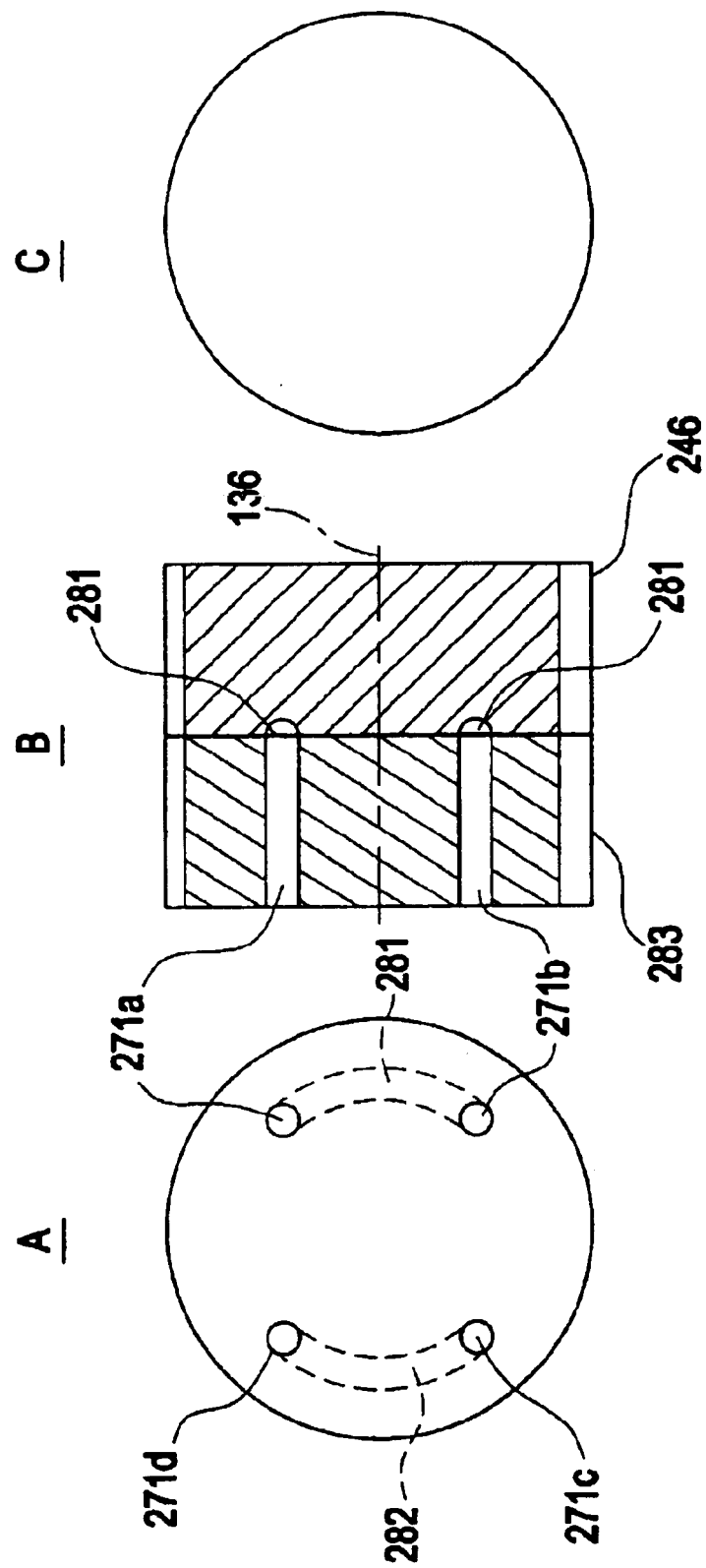
FIG. 6. Schematic drawing of selected portions of a switching valve. A. A first side planar view. B. A sectional view. C. A second side planar view.

Rotary switching valve 61 is schematically shown in FIG. 6. The valve comprises, in a first valve unit 283, a circular array of four peripheral ports 271a–271d and, in a second valve unit 246, further comprises connector channels 281 and 282 In FIG. 6, a continuous switching channel is created by peripheral port 271b plus connector channel 281 plus peripheral port 271a. A continuous switching channel is also created by peripheral port 271c, plus connector channel 282, plus peripheral port 271d. The second unit 246 is rotatable about its main axis (imaginary line 136) under the control of the computer 17, so that connector channel 281 can form a continuous switching channel with, peripheral ports 271a and 271d. In the latter situation, channel 282 forms a continuous switching channel with peripheral ports 271b and 271c.

A rotary valve combination 59 comprising a rotary selector valve 51 connected by its common central port 241 via a conduit means 121 (e.g., a tube or capillary with an internal passage 122) to the peripheral port 271c of a rotary switching valve 61 is shown schematically in FIG. 11.

EXAMPLE

Materials

Here, we report development of a novel instrument with miniaturized reaction cartridge and conversion flask (each about ⅒th the size of a high-end commercial instrument—Applied Biosystem's model 494cLC) and reagent/solvent flow paths. Our sequencer allows identification of amino acid derivatives well below 50 femtomoles, with repetitive yields in the 90–94% range; chemical background is very low. Because the instrument incorporates a miniature, pressurized flask with glass capillary pick-up line, it could conceivably be interfaced with continuous-flow, nanospray-type mass spectrometry, as recently reported,[31] for mass analysis of any peptide or amino acid derivatives. The position of the mass spectrometer would be the same as the HPLC column in FIG. 1.

All reagents and solvents (see also FIG. 1), PTH-amino acid standard, β-lactoglobulin standard, polybrene ('biobrene'), glass fibre discs, and cartridge seals were obtained from Applied Biosystems (Foster City, Calif.), except where noted. Acetonitrile was from Burdick & Jackson (Muskegon, Mich.), PTH-norleucine from Pierce (Rockford, Ill.), and the highest purity argon and helium gas from TechAir (White Plains, N.Y.).

Microfluidics Sytem: Edman Chemistry Configuration

Figure 1B:
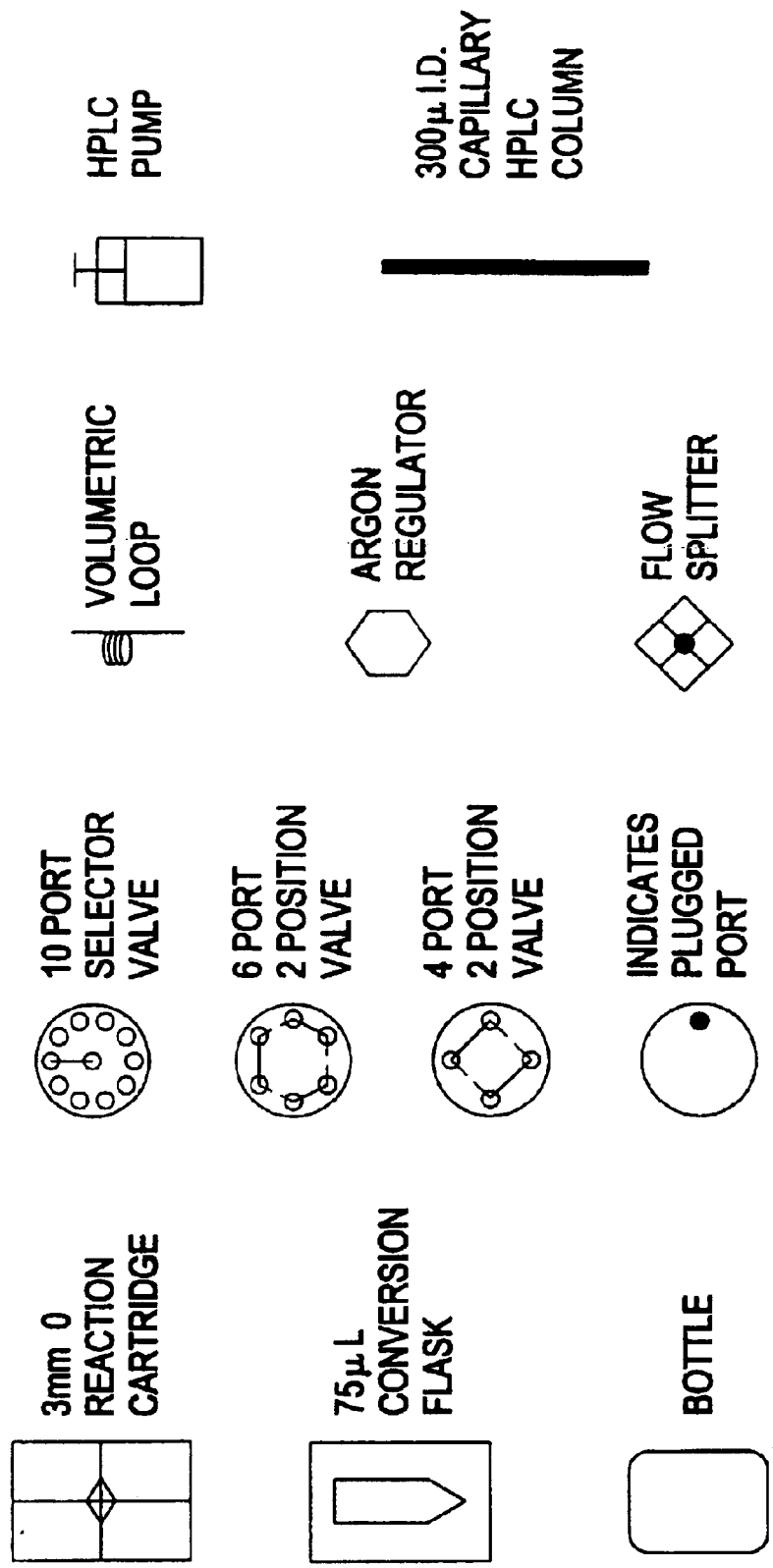
Figure 2B:
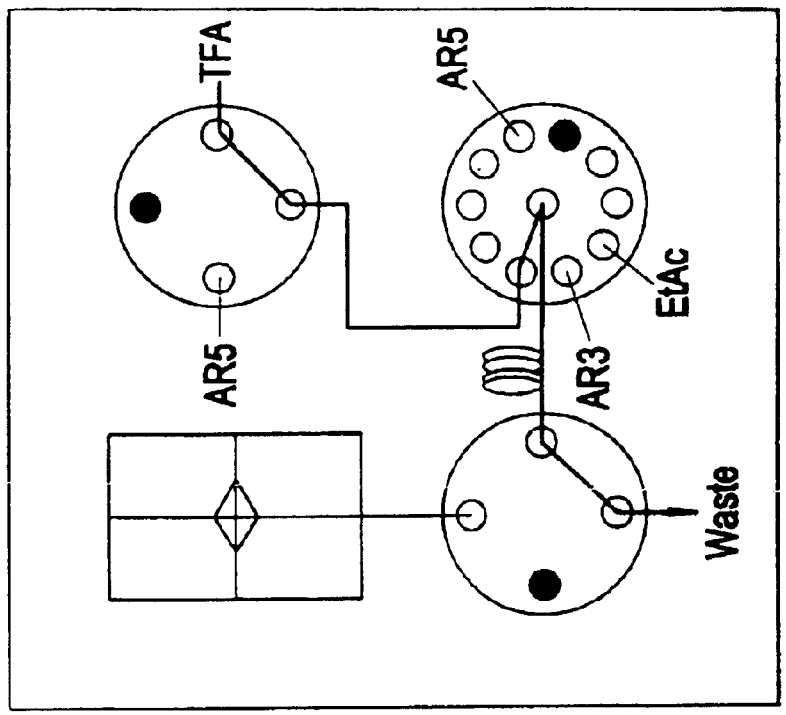
FIG. 2. PSMSK 'function #29', deliver liquid TFA to cartridge. This function consists of the seven sequential 'events', i.e. unique valve position combinations, as shown in panels A–G and listed in panel H where events 1–7 correspond to panels A–G, respectively. Only rotary valves 51, 61, 66 are shown; for the precise positioning in the entire system and for the key to symbols and abbreviations, see schematic in FIG. 1. Valve 51 is a ten-port selection and valves 61, 66 are two-way switching (A/B); solenoid valves (not shown) are used to pressurize or vent the TFA bottle (ON/OFF). The flow path through the valves during each event is shown in bold; no liquid or gas flow occurs during 'event #7'. Total function time is 1 min 44 sec. 'Function #29' is used in the reaction cycle (Table 2A) as step 30.
Figure 2A:
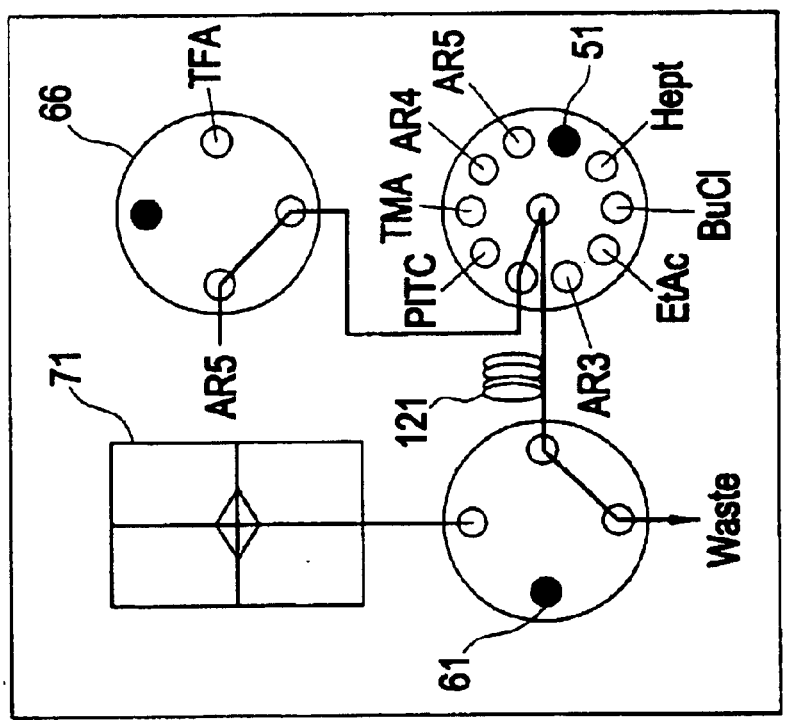
Figure 2D:
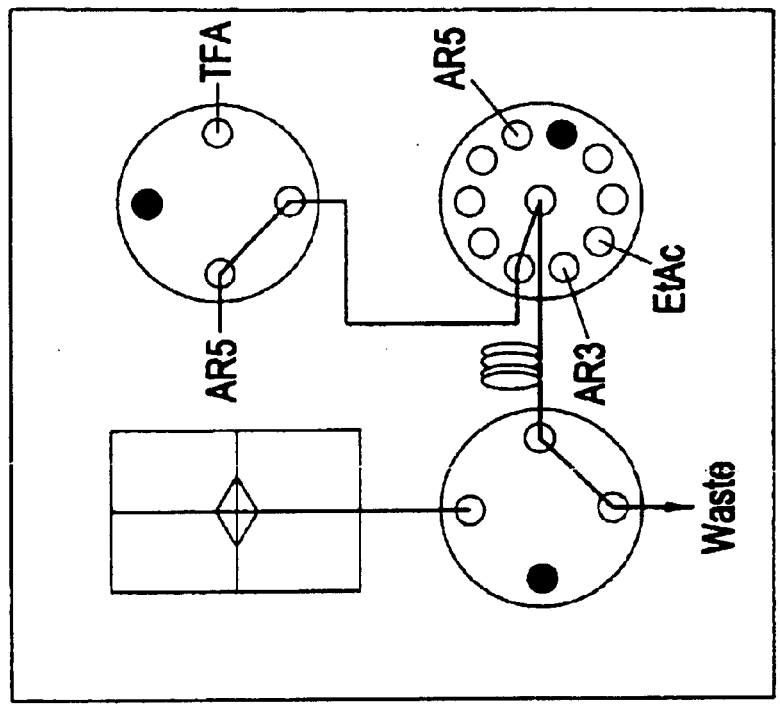
Figure 2C:
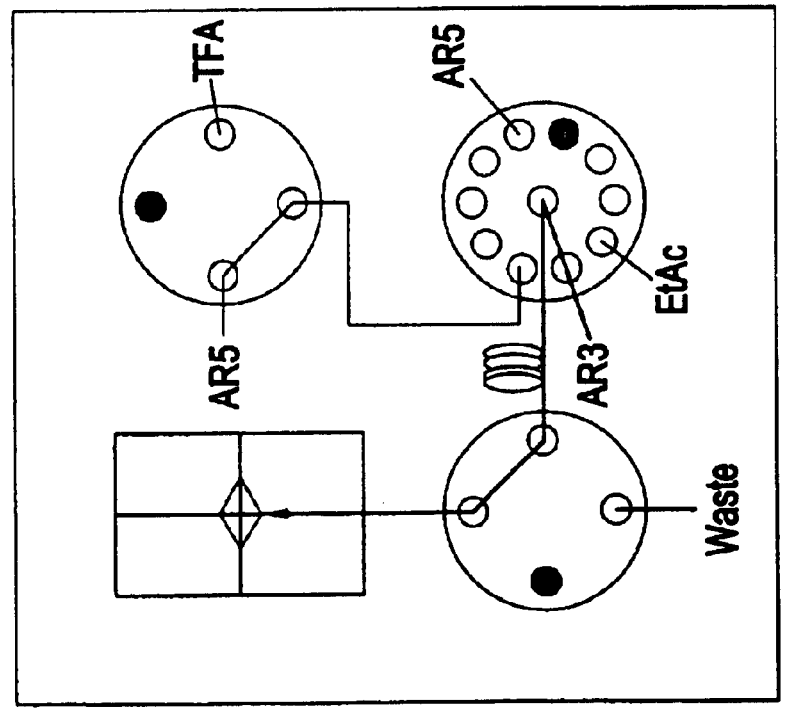
Figure 2E:
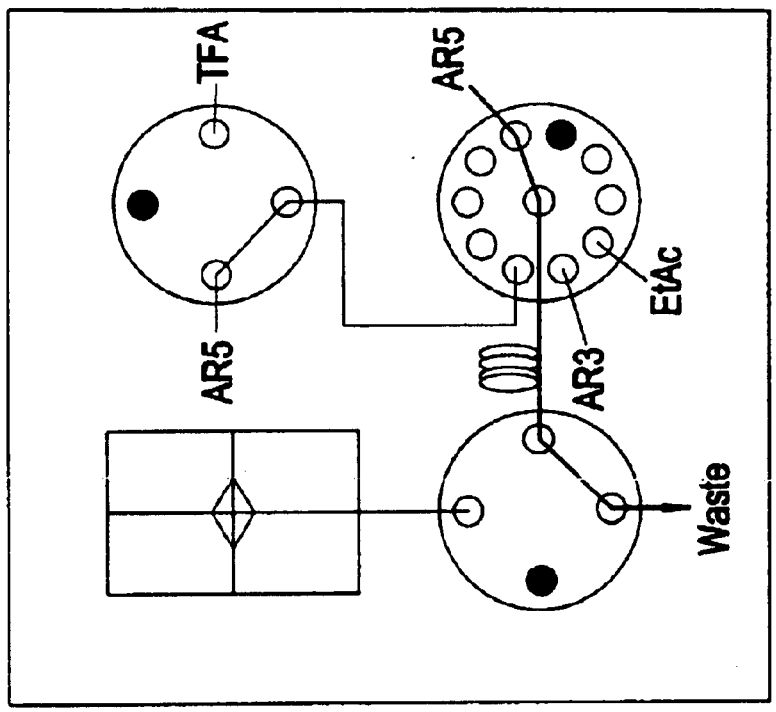
Figure 2F:
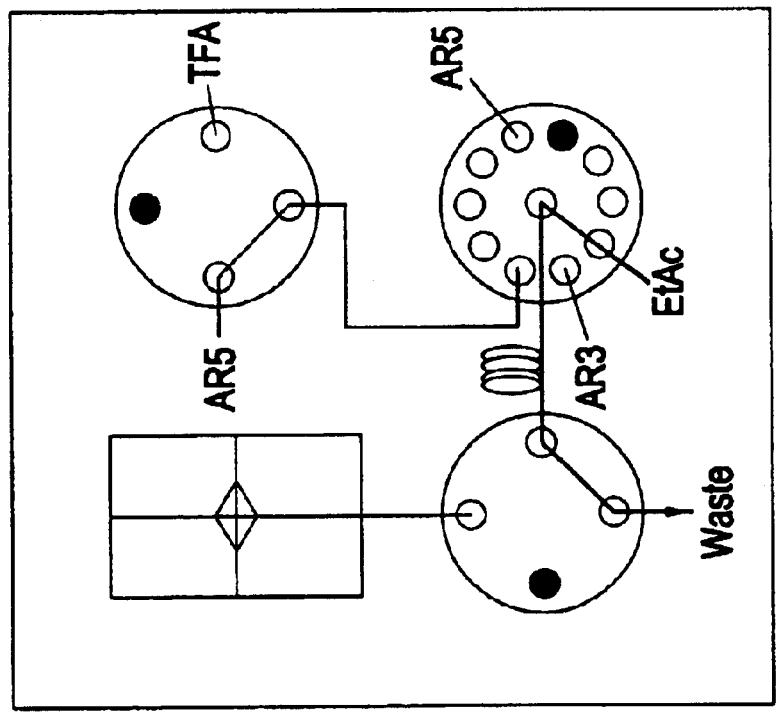
Figure 2G:
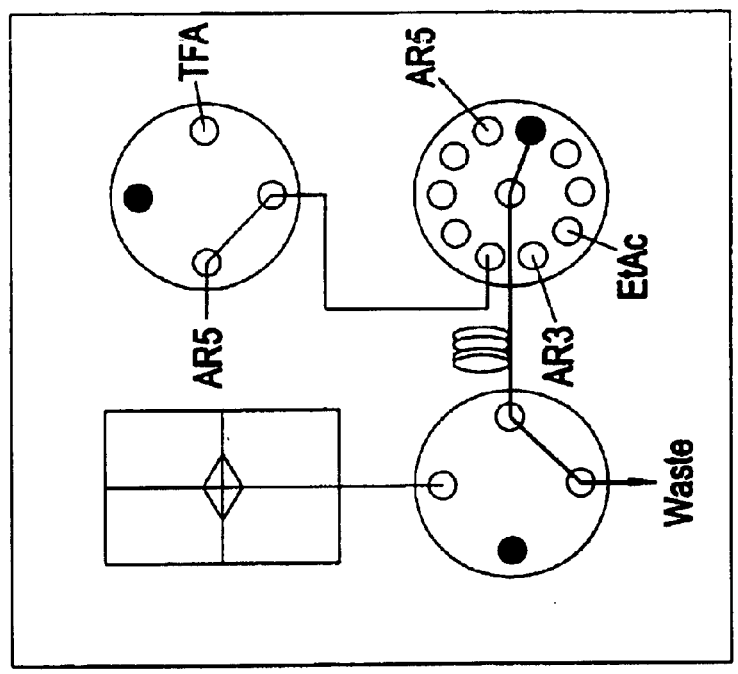
Figure 2H:
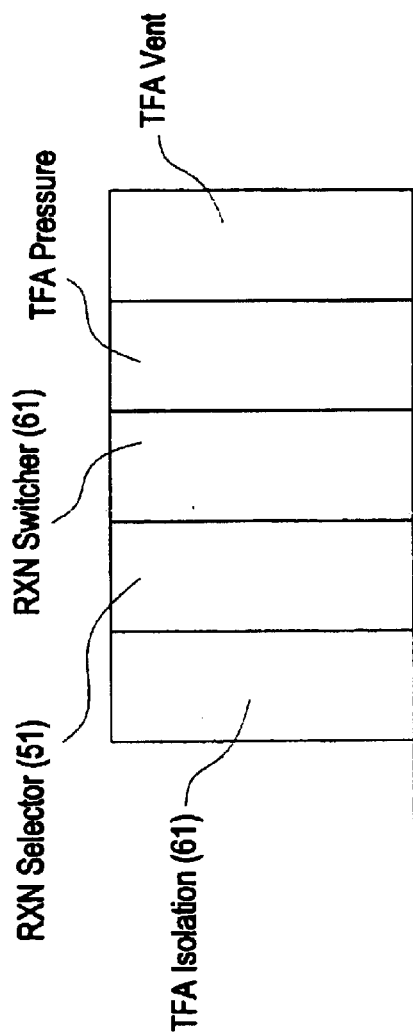

The automated micro-fluidics system 100 (also referred to as the "PSMSK sequencer" or simply "PSMSK") can be better understood in relation to FIG. 1. The system is built around an array of eight rotary valves, connected with fused silica capillary (50, 75, 100, and 150-μm I.D./365-μm O.D.; Polymicro Technologies; Phoenix, Ariz.) to two miniaturized reactors, a reaction cartridge (functioning as a reaction vessel) 71 and a conversion flask (or conversion vessel) 101 (see FIG. 1). The system has an extremely low internal volume of all components in the fluid path (see Table 1), which makes possible the automated precision metering and delivery of reagents in the sub-microliter range.

Cheminert series (Valco, Houston, Tex.) rotary valves were chosen for the fluid system because of their low internal volumes, small size, and ease of computerized control. These valves have 150-μm port diameters and a total internal volume of less than 0.4 μL. By mounting the valve rotor seal with a lower torque, greater longevity is obtained at a sealing pressure of 250 psi (instead of a normal factory-rated 5,000 psi). The wetted surfaces are fabricated out of the inert polymers, PAEK and Valcon E. PEEK nuts and one-piece fused silica adapter ferrules (Valco #ZN1FPK-10, ZF1PK) are used to connect fused silica capillary to the valve ports. Two basic categories of rotary valves are used in the system. The multi-position selector valve is characterized by a central common port and a circular array of peripheral ports positioned at the outer circumference of the valve stator. A rotor seal 245 with a single radial fluid path connects the central common port to one of the peripheral ports, determined by the angle of rotation. Ten-port port valves 52 and 51 of this type (FIG. 5) are used as a conversion selector valve 52 and a reaction selector valve 51 respectively to select reagents and argon gas for delivery to the conversion flask and reaction cartridge, respectively (FIG. 1). Two-position switching rotary valves have ports positioned around the outer circumference of the stator only (FIG. 6) The rotor seal 246 in a switching valve typically has more than one notch and connects adjacent ports in an arc shaped path. Six-port switching valves 64 and 63 are used as an injector valve 64 and a flask valve 63. Four-port switching valves 61, 62, 65, 66 are used as transfer valve 62, conversion switching valve 65, TFA isolation valve 66, and reaction switching valve 61 (See FIG. 6). To create the specialized flow paths for Edman chemical sequencing and to eliminate any dead volumes in the system, many of the switching valves incorporate rotors (rotor seals) that are custom fabricated as to their number of fluid paths. (Valco, Houston, Tex.). Valves 65, 66 and 61 have rotors with only one fluid path instead of the standard two; the rotor of valve 63 has two fluid paths instead of the standard three. Ports that are unused are plugged with PEEK nuts and solid Teflon tubing (Zeus, Orangeburg, S.C.).

By connecting the common port of a selector valve via a capillary to a peripheral port of a switching valve, the connecting capillary may serve as a precision metering loop. (FIG. 11) This arrangement is used to deliver consistent volumes of reagents to both the reaction cartridge and the conversion flask 101. For instance, the reaction selector valve 51 is coupled to the reaction valve 61 with a section of capillary that forms a 0.5-$\mu$L loop 121, used to meter liquid TFA and PITC to the reaction cartridge 71 (FIGS. 1 and 11). The conversion selector valve 52 is coupled to the conversion switching valve 65 with a section of teflon tubing forming a 7.5-$\mu$L loop 124, used to deliver a metered volume of PTH-amino acid standard, 25% TFA, and 10% MeCN to the flask 101 (FIG. 1). It is especially useful for the consistent injection of sample to the HPLC system. The use of this metering loop is described further below.

Each valve has its own integral microelectric actuator for precise control of rotation with a 100-msec switching time (actuator not shown in the Figures). The instrument control software sends simple ASCII commands via standard RS-232 serial communication to control the actuator position. Each valve is programmed with its own unique identity number. The commands are prefaced with this I.D. tag, allowing the control of several valves simultaneously over one daisy-chained serial connection. Since the valve rotation is bi-directional, the valves are initialized by the software to take the shortest possible rotation path when switching between ports. This feature is considered strategically when programming valve functions to ensure that certain chemicals (i.e. TFA and TMA) never mix (see FIG. 2).

The current system includes twelve 40-mL bottles 1–6, 41–44, 181–2 for a wide range of customized chemistries. Each bottle is pressurized with argon gas through an inert teflon solenoid valve (Angar Scientific; Cedar Knolls, N.J.) controlled by logic signals from the instrument control software of a computer 17. Inert PEEK check valves (Lee Company, Westbrook, Conn.) are fitted on the bottle pressure lines to ensure that chemicals do not contaminate the argon regulation system.

There are six argon regulators 171a–171f that are in gas sources and which provide argon at pressures of 2.0, 2.0, 4.0, 12.0, 24.0 and 50.0 psi, respectively. (Porter Company, Hatfield, Pa.) (see FIG. 1). Two are dedicated to pressurizing the TFA bottle 3 and TMA bottle 2; the remaining four are available for supplying the other bottle positions, for providing varying levels of pressurized argon to deliver reagents to the reactors, and for drying operations. The pressure of each regulator is monitored by a chip-based pressure transducer (SenSym, Milpitas, Calif.) and displayed in the instrument status window on the computer.

Reaction Cartridge

Figure 7:
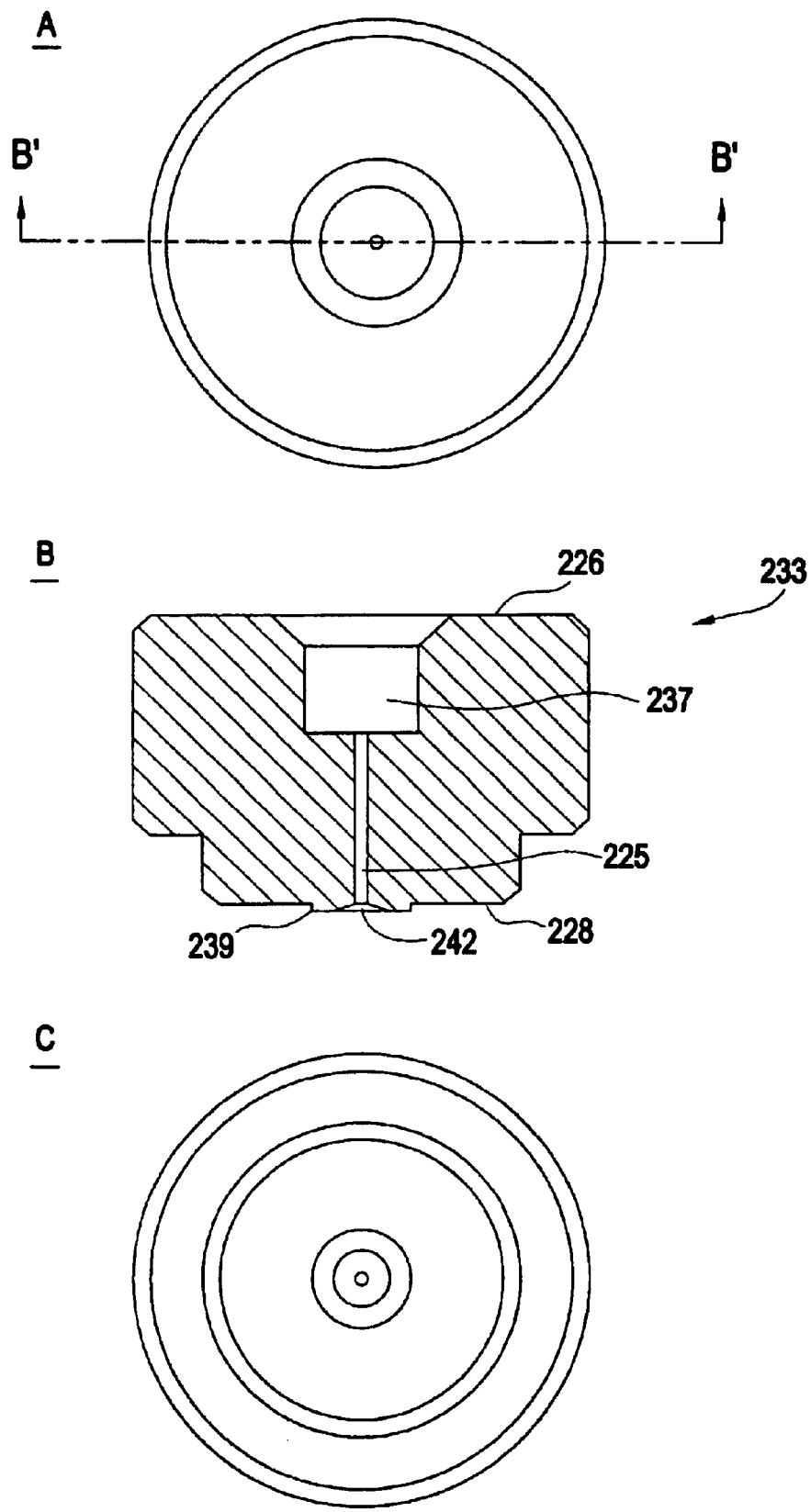
FIG. 7. Top Block of reaction vessel. A. A planar view. B. A sectional drawing along the line B'—B' in A. C. A bottom planar view.
Figure 9:
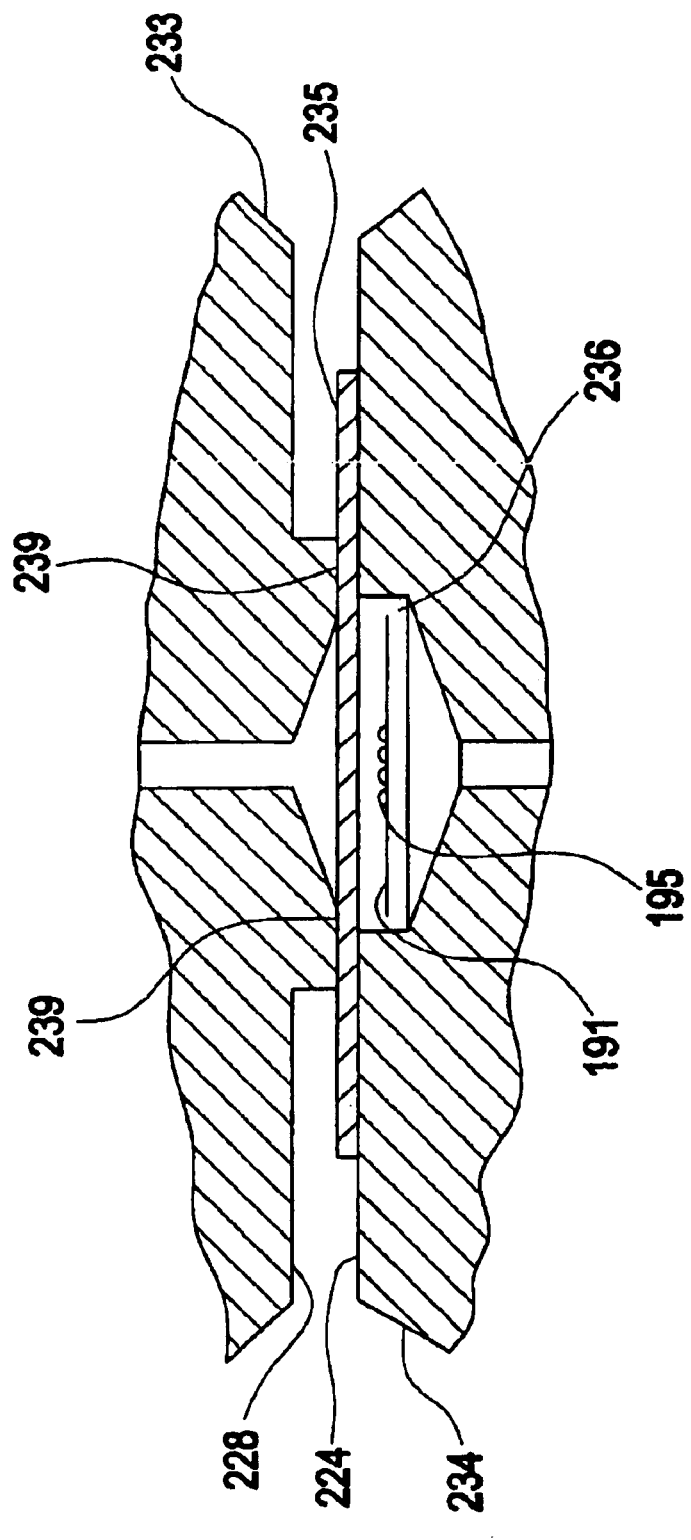
FIG. 9. Schematic sectional view of reaction vessel chamber and contents created by combining the bottom block (FIG. 8) and top block (FIG. 7) of the reaction vessel with additional components.

There are two reactors in the system when configured for Edman chemistry, a flow-through 'reaction cartridge' 71 and a solution chemistry 'conversion flask' 101 (FIG. 1). Various features of the reaction cartridge are shown schematically in FIGS. 7, 8 and 9. The reaction cartridge 71 consists of two 0.5-inch diameter/0.5-inch high cylindrical blocks 233 (FIG. 7) and 234 (FIG. 8), manufactured out of borosilicate glass (United Lens; Southbridge, Mass.), stacked vertically to form the reaction chamber. Both blocks were bored with a 0.015-inch fluid path 225 through the central axis. One flat face 226, 227 of each block was machined with a 0.25-inch cylindrical cavity 237, 238 for a pressure fit tubing connection utilizing a ferrule. The second flat face 224 of the bottom block 234 was machined with a conical cavity 226 contiguous with a 3-mm circular cavity 236 to hold a glass fiber support membrane 191 for immobilizing the protein (FIG. 7). The second face 228 of the top block 233 was machined with a complimentary mating surface including a rim 239 that seals precisely around the circumference of the glass fiber disc with the use of a permeable Teflon seal 235 (See FIG. 9). The second face 228 was also machined to include a conical cavity 242.

The cartridge 71 is assembled in an aluminum heater (not shown) that is thermostatically regulated by the instrument control software. The heater has a window and neon back lighting to view the contents of the cartridge. The top block 233 is held captive inside the reaction cartridge assembly at all times. It is only removed for occasional cleaning. For sample loading, the bottom cartridge block 234 is removed from the assembly in a stainless steel holder with a simple "half-twist" mechanism. Once the protein 195 has been pipetted on the disc 191, a permeable teflon seal 235 is placed on top of the bottom block 234 (See FIG. 9). The cartridge 71 is then fully assembled by mounting the stainless steel holder (not shown) to the heater with a second half-twist. A spring steel bellville washer is located at the top of the cartridge to ensure a tight seal while preventing the glass blocks from damage during the assembly. The cartridge is pressure tested prior to all sequencing runs to ensure that the reaction chamber is an isolated, oxygen-free environment, minimizing background artifacts produced during the coupling and cleavage reactions.

There are two rotary valves 61 and 62 that control flow through the reaction cartridge. Located at the bottom of the cartridge is the reaction switching valve 61, that controls delivery of reagents and argon gas from the reaction stream selector valve. The direction of flow during the sequencing chemistry is from the bottom upward through the sample carrier. The transfer valve 62 at the top of the reaction cartridge is a two position switching valve, that directs the outlet of the cartridge to the conversion flask: for further processing or to the waste bottle.

Conversion Flask

Figure 10:
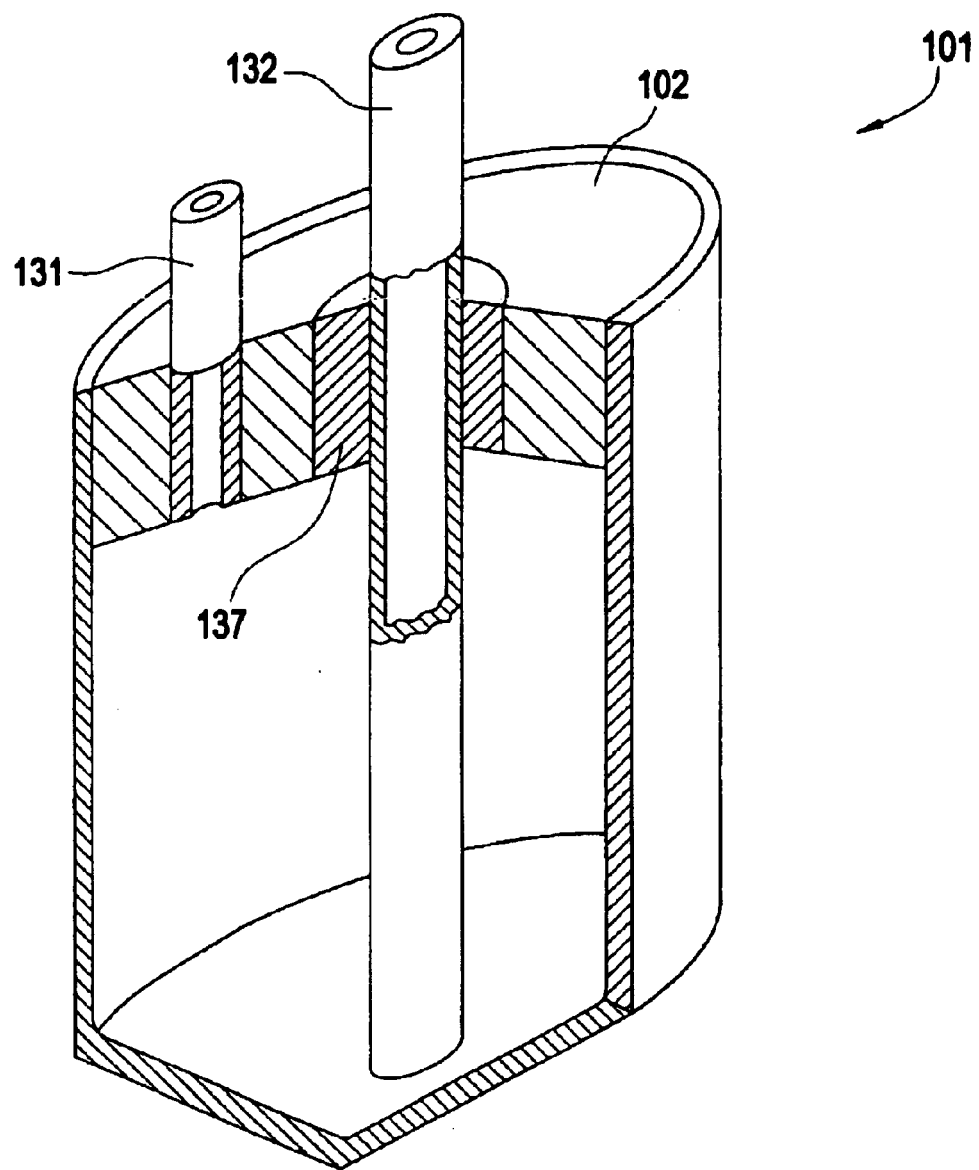
FIG. 10. Schematic partially sectional drawing of selected portions of a conversion flask.

The conversion flask 101, illustrated schematically in FIG. 10, is a, 96-$\mu$borosilicate tapered glass vial (Pierce; Rockport, Ill.). It is mounted inside an aluminum heater (not shown) thermostatically regulated under the control of the computer 17. Tubing connections are made to the flask through a teflon seal 102 at the top. The vial can be removed easily from the heater for cleaning or exchange by unthreading a stainless steel thumbscrew located at the bottom of the assembly. There are two tubing connections 131, 132 to the flask 101. The first is a vent line 131 made from $\frac{1}{16}$-inch O.D./0.004-inch I.D. teflon tubing. It is installed with a simple pull-through friction fit through a 0.056-inch hole in the teflon seal. The vent line is cut flush with the inside of the teflon seal using a razor blade. The second tubing connection to the flask is a pickup line 132 made out of 75-$\mu$m I.D./365-$\mu$m O.D. Polyimide coated fused silica capillary. To install the pickup line first a 0.01-inch I.D./ 0.0625-inch O.D. teflon tubing sleeve 137 is pulled through a 0.056-inch hole in the teflon seal at the top. This sleeve is cut off flush with the inside of the teflon seal using a razor blade. By pulling the capillary 132 through the teflon sleeve a pressure tight seal is formed. A long enough section of capillary is pulled through the teflon seal so that it reaches the bottom of the flask. A bunsen burner is used to burn off the polyimide coating from the portion of the pickup line that is exposed to reagents, as it was found that the polyimide breaks down during the conversion process and interferes with the liquid chromatography.

A 6-position, 2-port switching valve 63 (see FIG. 1) is located above the flask 101 and controls the delivery of fluids and argon gas. In position A, the vent is opened to waste and the pickup line 132 is connected to the transfer valve 62. This position is used to deliver fluids to the flask 101 in a controlled fashion from the bottom up, and also to bubble argon through the sample. This argon dry operation is used in many situations, including the conversion of ATZ-amino acids to their PTH counterparts, solvent evaporation prior to HPLC injection, and high pressure flask cleaning between cycles. In position B, the vent line 131 is connected to the transfer valve 62 and the pickup line 132 is connected to the injector valve 64. This position is used to empty the contents of the flask 101 to the injector loop 123 or the waste bottle 201. By delivering pressurized argon from the reaction selector valve 51 to the vent line 131 the contents of the flask 101 are forced out through the pickup line 132.

A 10-cm long, 50-$\mu$m I.D. restrictor capillary 134 is connected to the outlet of the injector valve 64. The narrow internal diameter of the restrictor capillary provides sufficient back pressure to maintain a gradual 15 second loading of the injector loop 123 when argon at 12.0 psi from gas source 171d is used to pressurize the flask. The low internal volume of the restrictor capillary is also conducive to a high injection percentage. When the first sign of liquid is present at the end of the restrictor capillary, only 0.2-$\mu$L of sample has passed beyond the loop. This makes it possible to routinely inject 5 $\mu$L out of a sample volume of 7.5 $\mu$L.

HPLC System

PTH-amino acids are separated on a 25-cm long, 300-$\mu$m I.D. capillary HPLC column, 151 custom packed (LC Packings, San Francisco, Calif.) with 5-$\mu$m $C_{18}$ PTH stationary phase. The column 151 is placed inside a heated enclosure (Eppendorf; Westbury, N.Y.)) and thermostatically regulated at 55° C. HPLC solvent A 221 is 5% tetrahydrofuran in water, with 20 mL of 'Premix Buffer' added per liter (Applied Biosystems); solvent B 222 is acetonitrile (Burdick & Jackson) with 500 nmol of dimethylphenylthiourea (DMPTU; Applied Biosystems) added per liter. Solvents are contained in Kontes Ultraware (Vineland, N.J.) reservoirs 181 and 182 and are sparged with helium gas at a pressure of 3 psi. The gradient is formed by an Applied Biosystems 140D micropump at a flow rate of 30 $\mu$L/min; a flow splitter (LC Packings) with a 10:1 split ratio delivers a consistent gradient (12–24% B/4 min; 24–50% B/22 min; 50–90% B/1 min) to the column at a flow rate of 3 $\mu$L/min. The flow splitter 232 also contains a micro-volume union and static mixer. The outlet of the column is directly connected to a UZ-View 'ball lens' capillary flow cell (LC Packings) which is mounted in an Applied Biosystems model 785A UV absorbance detector. All connections in the LC system are made with 75-$\mu$m I.D./365-$\mu$m O.D. fused silica capillary. The detector is set to a wavelength of 269 nm, with a rise time filter setting of 2 sec. The absorbance data is collected from the UV detector by a Nelson 900 Series analog to digital converter, filtered, stored, and analyzed using TurboChrom 4 software (PE Nelson; Cupertino, Calif.).

Instrument Control

The instrument 100 is controlled by a computer 17, a Macintosh 225 MHz computer (Apple; Cupertino, Calif.) comprising and running a software application, which was programmed in the LabView environment, version 5.1 (National Instruments, Houston, Tex.). A DaqCard 1200 (National Instruments) data acquisition and control card is installed in the computer and is used to interface between the software and circuit board contained in the instrument enclosure. The DAQ card has 8 analog to digital (A-D) converters and 24 lines of digital input/output. The A-D converters monitor the signals from the reaction cartridge and conversion flask temperature sensors as well as the argon regulator pressure transducers. The digital lines control the solenoid valves, reaction cartridge and conversion flask heater elements, and four relays used to control external devices (e.g. HPLC pump, UV detector, and data collection system). The rotary valves are controlled by serial communication directly from the computer's serial port. Communication from the computer to the sequencer is accomplished through one DB-9 RS-232 serial cable and one 50 conductor ribbon cable. These connect to ports on the back panel of the instrument. Also located on the back panel are a cooling fan, bulkhead connection for the waste bottle vent line, and the four relay outputs for controlling external devices.

The circuit board is multifunctional. It buffers the low millivolt signals from the pressure transducers and temperature sensors and converts them to the useable range of the DAQ card A-D converter. The 5 VDC digital logic signals from the DAQ card trigger transistors on the circuit board to switch higher current power to the solenoid valves, relays, and heater elements. In the case of the solenoid drivers, an additional circuit drops the initial 24 VDC 'strike' voltage down to 12 VDC after 100 msec. The board also acts as a voltage regulator, supplying the correct power to the instrument's cooling fan and neon lighting. The circuit board was created from a copper clad board with a 'photo-resist'" coating (Kepro Circuit Systems, St. Louis, Mo.). A negative of conductor circuitry, designed with CAD software, was printed on a transparency, and placed on the board, after which the board was exposed to UV light in a darkroom. Hot sulfuric acid was used to etch away unneeded copper, leaving the desired conductor circuitry.

The Lab View software environment allowed the design of a graphical display that emulated the actual operation of the instrument. The status of all valves, relays, regulator pressures, and temperature transducers are displayed on the monitor screen 18 in real time as the instrument is operated. The software has two modes of operation, manual and automatic. In both modes the same real time graphical display is utilized. In the manual mode a manual control window is also present on the computer desktop. This window contains buttons for the control of every piece of hardware at the user's discretion. In the automatic mode, control cycles are preprogrammed by the user. In this case, the manual control window is replaced by a sequencer status window that displays information regarding the current sequence, cycle, and function being performed.

An automated control program is created through the use of user-defined reaction and conversion functions (see Table 2). A sequencer cycle is one complete program for analyzing one amino acid residue of the protein. Distinct reaction and conversion cycles are created independently to control the activity of the two distinct reactors 71, 101. The software then meshes these two cycles together automatically so that the transfer of sample between the reaction cartridge 71 and conversion flask 101 is coordinated properly. Several cycles are looped together to create a sequence program that can process as many amino acid residues as the user requires. Sequencer functions are not necessarily single command events. A function can include as many independent timed 'events' as needed. In fact, nearly all of the functions we used were more than one event, with a maximum of eight events. This feature is especially useful since most of the chemistry is automated with the use of metering loops. Delivering a loop of reagent is a multi-step procedure, as illustrated by the metered delivery of TFA liquid 13, the most complex case, in FIG. 2.

Operation

The reaction cartridge 71 was designed with a 3-mm diameter disc 191 to reduce chemical and amino acid background, a requirement to call amino acid sequence from the chromatographic data. Yet, the size should be large enough to allow for a practical sample loading volume. At a diameter of 3 mm, a glass fiber disc can hold a sample volume of 2 $\mu$L. Several 2-$\mu$L loads to a single filter can be done in series to accommodate samples of larger volume.

Prior to sample loading, the glass fiber disc 191 is coated with 0.18 mg of polybrene, a polymeric sample carrier that increases the protein affinity for the glass fiber. The unloaded, polybrened disc is then precycled by running several standard sequencing cycles until the chromatogram appears clean. BLG protein standard was pipetted onto the disc, dried using 2-psi argon gas, and the reaction cartridge was reassembled and pressure tested. The reaction and conversion cycles (Table 2) were initially based on the custom cycles used with commercially available sequencers in our lab.[17] They have since been extensively modified to meet the requirements of the new miniaturized flow path and adjusted according to experimental observations.

Table 2A illustrates in detail reaction cycle #27 "Glass Fiber Disc". Steps 1–II comprise the coupling of PITC 11 to the N-terminal amino acid of the protein. TMA vapor 12a originating at 2 psi from solution 12 is delivered three distinct times, at 400 seconds each, for a total of 1200 seconds. TMA provides the basic environment necessary for proper coupling. Deliveries of 1-$\mu$L aliquots of 1% PITC 11 are interspersed between the TMA steps. The overall coupling time in the reaction cycle was set intentionally long to ensure minimal sequencing lag that would otherwise result in inefficient coupling chemistry. This is then followed by a series of solvent washes (Steps 12–29) with heptane 141, ethyl acetate 142, and butyl chloride 143. The volume of the washes was optimized to minimize chemical background while preventing sample washout (see Table 1). For subsequent acid cleavage (Step 30), delivery of TFA 13 was also tightly controlled, as to achieve low lag while minimizing sample washout. We found that a volume of 0.5 $\mu$L was most effective. This step is described in detail in FIG. 2. Transfer of ATZ-amino acids to the conversion flask 101 (Steps 36–55) was the subject of rigorous optimization. Since the volume of the flask is only 75 $\mu$L, solvent volume should balance efficient extraction of the ATZ-amino acids with this limitation. Thus, the delivery of the transfer solvent (BuCl 143) was broken up into several smaller steps, with argon dries interspersed between, to keep the solvent in the flask at a manageable level. This procedure also increases the efficiency of the extraction, as shown.[17] Following the transfer phase, the reaction valves are cleaned with BuCl, 143, Heptane 141, and EtAc 142, to prepare them for the next amino acid cycle (Steps 58–61).

Table 2B details the conversion cycle utilized, #28 "Low Pressure Conversion". It begins with an extensive cleaning of the flask 101 (Steps 1–10) with 25% TFA/H2O 14 and 10% MeCN/H2O 144 to eliminate any carryover between cycles. The cleaning solvents are delivered through the vent line 131, instead of through the pickup line 132 as is the case with other deliveries during the sequencing run, ensuring better cleaning of all fluid pathways. Once filled with 40 $\mu$L solvent, the highest available argon pressure (50 psi) from gas source 171f is bubbled through the pickup line 111+132/ lower section to vigorously wash the entire internal volume of the flasks, including the top teflon seal and the highest reaches of the vial. The flask valve 63 then switches position so that high pressure argon is delivered to the vent 131, forcing the contents of the flask 101 to the injector waste 201. To expedite the large volume deliveries of 25% TFA/ water 14 and 10% MeCN/water 144 through the vent line, these bottles are pressurized with argon at 12.0 psi from source 171d. After cleaning, a 225-femtomole, 7.5-$\mu$L aliquot of PTH-norleucine 16 is added to the flask and evaporated (Steps 11–12). Then, a 7.5-$\mu$L loop load of the conversion reagent, 25% TFA/water 14, is delivered to the flask 101 (Steps 13–14), just before the transfer of ATZ-amino acid from the reaction cartridge 71 (Step 15). Argon at 12.0 psi is bubbled through the flask 101 for better conversion reaction kinetics and to slowly evaporate off the 25% TFA (Step 16). Once the flask 101 is completely dry, the injector loop 123 is flushed with argon to prepare for injection (Step 17), and the contents of the flask 101 reconstituted with a 7.5-$\mu$L loop of 10% MeCN, and bubbled with argon from source 171e at 24.0 psi to improve dissolution (Steps 18–22). Argon at 12.0 psi is then delivered to the vent line 131, displacing the sample into the injector loop 123 (Step 23). After 15 seconds, the injector valve 64 switches position, injecting the sample onto the column 151 and a relay closes to start the HPLC gradient program (Steps 24–25).

RESULTS AND DISCUSSION

Proteins can be prepared, fractionated and detected at the femtomole level. Taking into account a 2 to 5-fold loss during sample handling, chemical structure determination must then be done with just 100–200 femtomoles of starting material. Our objective, therefore, was development of an automated protein sequencer whose range of operation would include that range. We sought to do so by further miniaturizing the entire fluidics system, including reaction vessels and the analytical component, capillary (300-micron ID) LC, all in a very proximate arrangement.

Preliminary Considerations

We first constructed a stand alone, modular capillary-LC system (see Materials and Methods). Flow rates, gradients and column temperatures were optimized for various column/solvent combinations as to yield the best possible resolution, highest signal/noise ratio (in general and for each PTH-aa in specific) and least baseline drift. In anticipation of 'on-line' sample injections from a sequencer, we studied tolerance for increasing MeCN concentrations (3 to 10%) in function of progressively larger injection volumes (0.5 to 20 $\mu$L). As 'sequencer-injected' samples may also contain trace amounts of TFA, its effects were also investigated. Initial attempts at optimizing operational parameters, injecting standards (20–100 femtomoles each of all PTH-aa) in an 0.5-$\mu$L volume of 3% MeCN/0.1% TFA, resulted in complete separation. Most PTH-aa's can be detected at the 20 femtomole level, with signal/noise ratios better than 1 to 5, and injections of up to 5–8 $\mu$L in volume appeared feasible (data not shown). Consequently, if analysis of 60–70% or more of the PTH-aa's after each cycle is desired, the analytes should be dissolved in less than 7–10 $\mu$L of solvent, in turn necessitating a smaller conversion flask; e.g. 75 $\mu$L, as compared to 750 $\mu$L in current commercial sequencers. Space constraints required the use of 75-$\mu$m I.D./365-$\mu$m O.D. capillaries for liquid delivery and pick-up. To avoid overfilling the smaller flask 71 during ATZ-aa transfer, the reaction disc 191 had to be reduced in size accordingly, to 3-mm diameter. Further reduction in wetted surfaces was accomplished by bringing chemistry vessels and detection system in close proximity, plumbed together with 50 to 100-micron ID capillary tubing as well, to create an integrated micro-fluidics system. Capillary bore tubing requires substantially higher pressures for delivering and drying liquids. Using a bread board instrument, it was found that increased back pressures cause liquids to back up in the wrong ends of the Z-path type valve blocks of an Applied Biosystems instrument. It was therefore decided to replace them with nanoliter-dead volume rotary valves in the final design, which also permitted accurate metering of reagents in the sub-microliter range.

Design and Construction

The instrument was constructed to conform to the stipulations summarized above and following the schematic diagram shown in FIG. 1. It features the incorporation of 8 rotary valves (numbered in FIG. 1). The reaction cartridge 71 is positioned between valves 61 and 62 (liquid and gas flow from the bottom up) and the flask 101 right below valve 63. Note that, together, valves 51 (10-port selection) plus 61

(two-way switching) accomplish the same result as the "cartridge reagent/solvent-blocks" in an Applied Biosystems automated sequencer (see also FIG. 2); similarly, valves 65 and 52 accomplish the same result as the "flask reagent-block" in an Applied Biosystems automated sequencer. Valve 66 (FIGS. 1, 3) serves to isolate TFA from the rest of the chemicals and solvents to exclude potential chemical problems, including salt formation upon contact with base (TMA). Rotary valves were selected on the basis of the lowest-dead volume and compatibility with TFA. Acid was continuously pumped through for an entire week without evidence of pressure leaks or visual damage. Cartridge 71, flask 101 and LC-injector valve 64 plus column 151 are all plumbed with glass capillary tubing; the rest with teflon capillary tubing.

The level of miniaturization and versatility incorporated in the design of our automated micro-fluidics system, as described here in the PSMSK sequencer, is best illustrated by comparison of the chemistry modules, selected wetted surfaces and variable pressurization to those in a state-of-the-art, commercially available sequencer (Applied Biosystems model "cLC494"). As shown in Table 1, the PSMSK reaction disc/chamber is about 4–8 times smaller, and eight-fold less reagent and considerably less solvent are consumed; however, wash solvent per disc surface area is comparable. The overall flow path volume(E-block to injector) is 30-fold smaller as compared to the cLC494. Available gas pressures range between 2 and 50 psi, whereas only from 1 to 3.5 psi in a commercial instrument. Most importantly, only the current system permits reproducible injection after every chemistry cycle of 67% of the end-products in a 5-μL volume, as compared to 55% in satisfying a critical requirement for the practical use of any 300-micron ID LC-columns.

Automation control software was written using Labview software on a Macintosh platform (details on software design package, digital control interface and computer are given in 'Materials and Methods'), and sequencer cycles (about 50–70 min in length; see Table 2) developed, allowing fully automated operation of the instrument 100. In addition to required temperatures, pressure regulation and gas flows, the program controls all rotary plus solenoid valves simultaneously and in a fully coordinated fashion; and allows to string together an essentially unlimited number of "functions" to create cycles of chemistry ("cycles"); which, in turn, can be looped together (i.e. repeated) 20 or more times. Any function itself consists of a particular sequence of unique valve position combinations ("events"), as illustrated in FIG. 2 for function #29, 'deliver liquid TFA to cartridge', a seven-event function. Here, sequentially, the reaction valves are flushed with argon, TFA metered and delivered to the cartridge, valves flushed, reaction selector valve rinsed with EtAc, flushed with argon and valves turned into 'safe' position (i.e. central channel in line with plugged port). Operational status can be monitored at all times through the use of a 'virtual instrument' graphical display that emulates actual instrument operation.

Operation and Fine Tuning

The prototype instrument 100 was fully tested for automated operation, followed by optimization of flows and chemistries, and then interfaced with a capillary HPLC system. To this end, precise optimizations of ATZ-extraction/delivery to flask and PTH-aa transfer from flask 101 to injector valve 64 were carried out, largely empirically, with the objective of reducing extraction and transfer volumes. Additional issues addressed were conversion chemistry (conditions of initial aqueous ATZ to PTC conversion, and TFA concentration for generating PTH-aa's), and dissolution (volume; % MeCN/% TFA) and volume reduction (forced argon evaporation) of the PTH-aa's. As a result, the system enables near quantitative LC-injection of volumes in the 5–10 μL range, making it fully compatible with capillary-LC.

Figure 3:
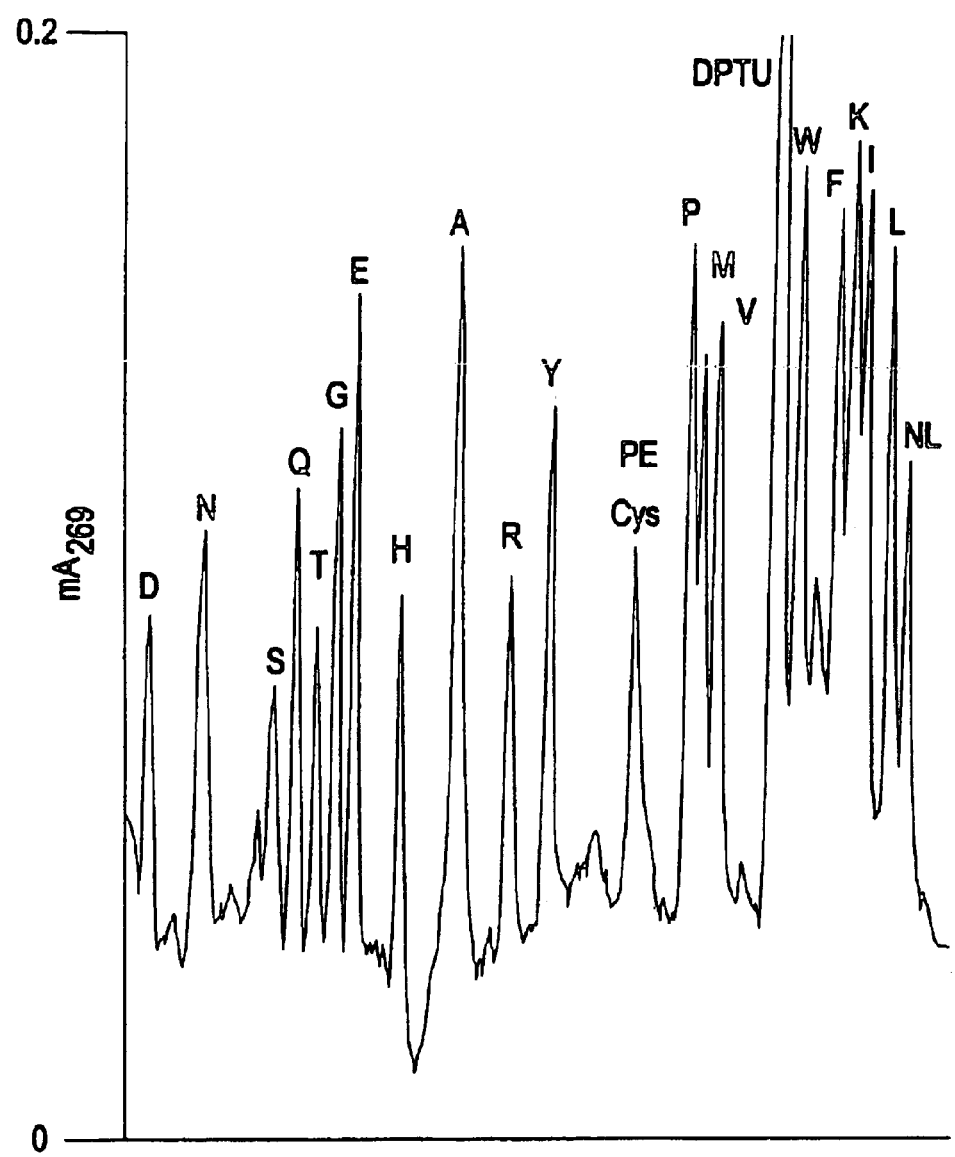
FIG. 3. 'On-line' capillary-LC analysis of 25 fmol (delivered to the flask) of PTH-amino acid standard under conditions as described in the text. A 300-micron i.d. column, packed with $C_{18}$ PTH (5-micron particle size) resin, was used at a flow of 3 $\mu$L/min; absorbance detection was done at 269 nm. Only the relevant portion of the chromatogram is shown. More details can be found in the 'Materials and Methods' section.

This is most convincingly illustrated in FIG. 3, where an LC separation of 25 femtomoles of PTH-amino acid standard 15 is shown. Note, that it concerns here 25 femtomoles of standard delivered into the conversion flask, dried down, redissolved, volume reduced by forced evaporation, and injected for analysis. We measured the final volume in the flask to be about 7–8 μL. Of that final volume, 5 μL (67%) is then normally injected, representing 17 femtomoles of standard mixture, assuming that no losses have occurred in the process.

Protein Sequencing

Following optimization of the individual chemistry and analysis modules, the integrated system was tested for micro-sequencing performance using, first, 1-pmole and then 400-fmole amounts of non-covalently attached protein standards. Changes were introduced to redress any observed problems until initial yields (i.e. recovery of the first amino acid) were consistently over 50%, repetitive yields (i.e. efficiency of the Edman degradation chemistry) in excess of 90%, and the predominant chemical background (i.e. DPTU) belong 1 piciomole per cycle. Several thousand cycles have since been completed without any major problems.

Figure 4:
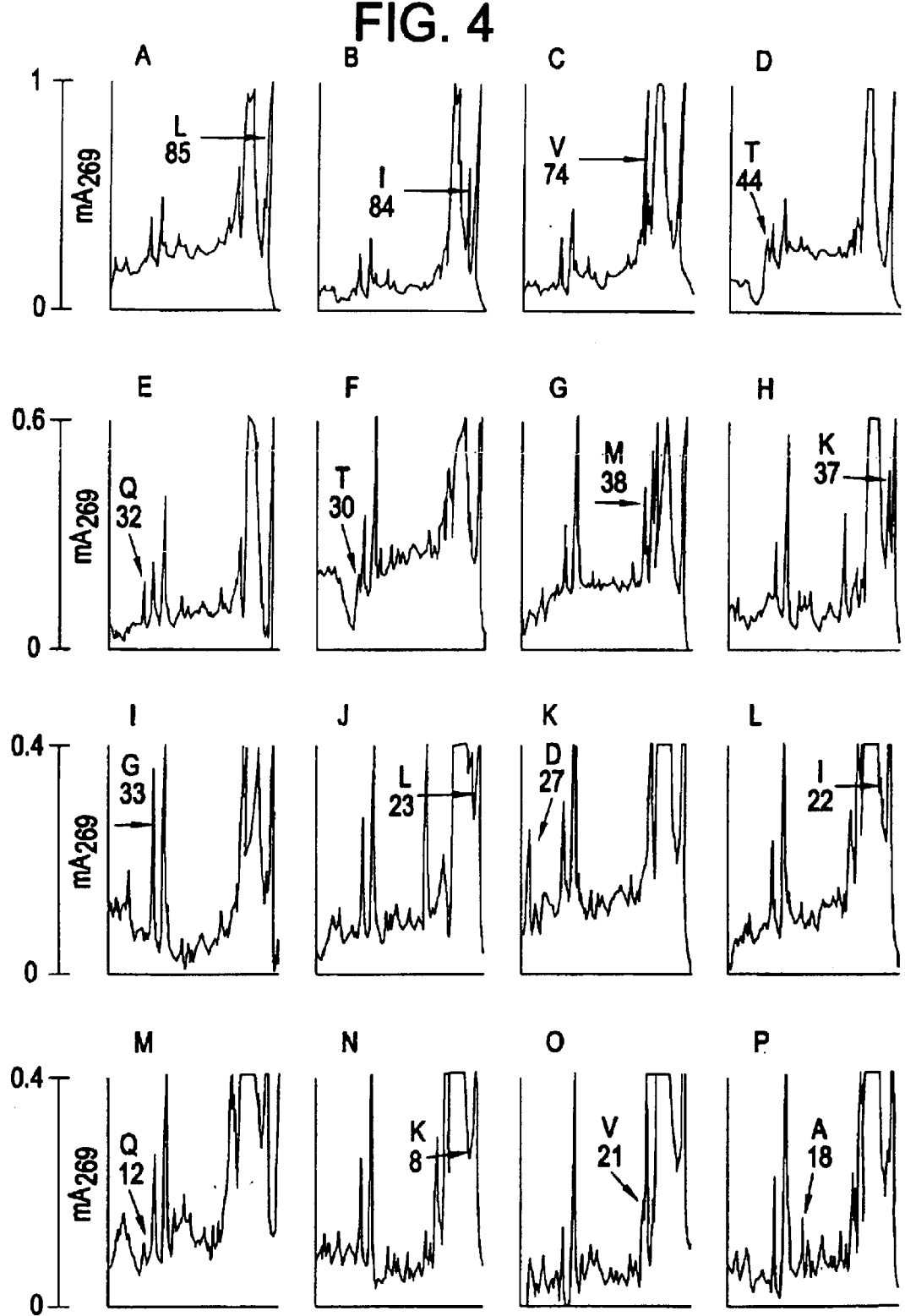
FIG. 4. Micro-chemical sequencing of 100 fmol bovine $\beta$-lactoglobulin using the 'PSMSK' microfluidics system and on-line, capillary-LC PTH-amino acid analysis. Experimental conditions were as listed under 'Materials and Methods' and in the FIG. 3 legend. Chromatograms 1–16 are shown; absorbance detection full scale varies, as indicated. PTH-amino acid peaks are indicated with an arrow and the femtomole amounts (corrected for background) shown.

An example of the PSMSK cyclic sequencing chemistry, using 100 fmoles of beta-lactoglobulin as starting material, is shown in FIG. 4. Although we recognize that the lower limits of sensitivity are being approached in this instance, the sequence can actually be called quite well by those skilled in the art, with the exception perhaps for Thr and Lys, residues known to recover at substantially lower yields during Edman degradation.[17] The initial yield was well over 70%, even after background subtraction; repetitive yield, as calculated from the background subtracted yields of PTH-Val in cycles 3 (74 fmoles) and 15 (21 fmoles), was 90.0%. By all means, this would be considered an acceptable result for any sequencing experiment in the event when a system's, any system's, lower limits of sensitivity have been reached. The difference being that in the example presented here, the amount of starting material was about eight to ten times less than hitherto reported for some of the more challenging high-sensitivity experiments using state-of-the-art commercial instruments.[19,23,24] Our result exceeds manufacturer performance specifications (i.e. 15 residues of 2 pmoles beta-lactoglobulin, with 92% repetitive yield)[19] of an Applied Biosystems cLC494 instrument by at least an order of magnitude.

The PSMSK instrument represents, therefore, a new phase in operative, Edman-chemical protein sequencing, both in terms of miniaturization and sensitivity. To put this advancement in some historical context, a brief overview of the Edman chemistry and its automation during the second half of the 20th century is given in Table 3.

Practical Considerations

To function as a truly practical and reliable device for elaborate, constantly repeated cycles of chemistries and analyses, be it process- or micro-scale, certain standard criteria of versatility and routine operation needed to be satisfied. Among PSMSK's most desirable operational features, we will briefly consider its durability and its capacity to utilize large numbers of reagents/solvents in an essentially unlimited sequence of reactions, extractions, drying steps, dissolutions, and transfers.

In the application-validated protein sequencer embodiment described above, ten different 'liquids' 11–16, 141–144 were transferred through diverse combinations of flow-paths and vessels, by using changing gas pressures and value position combinations, to carry out 86 discrete steps (61 in the reaction cycle; 25 in the conversion cycle—Table 1), totaling 227 'events' per cycle. While permitting a large degree of flexibility already, our automated microfluidics system could easily be upgraded to deliver dozens more of chemicals, through increasingly elaborate flow paths, by adding a few more multi-port selection valves. Such additions would be readily supported by the Labview-based instrument control software.

In cases of frequent usage, it is conceivable that dozens of 'cycles', hundreds of 'steps' and several thousand 'events' would be completed per day, totaling tens of thousands of valve rotations per week, and raising legitimate concerns about abrasion of rotary seals and resultant blockage or leakage. However, this is not what we have observed after more than a year of regular usage, comprising hundreds of thousands of discrete valve movements. Aside from offering some of the lowest internal dead volumes available, 'Valco Cheminert' microbore-type rotary valves (see 'Methods and Materials') have originally been designed to withstand pressures of up to 3,500 psi and could therefore be slightly loosened (e.g. factory calibrated to 200 psi) to accommodate a maximum pressure of 50 psi in our instrument, thereby extending life expectancies.

Finally, since the instrument is plumbed with capillary tubing, we took extra precautions to prevent salt crystal formation by separating acid and base in the microfluidics system at all times. This was most easily accomplished by isolating TFA 13 on a dedicated valve 66, in conjunction with proper rinsing of the exposed flow paths with EtAc 142 and flushing with argon from three different ports (see FIG. 2). As a result, no particulate-relating problems have ever been observed.

CONCLUSIONS

Detailed biochemical analysis of all molecular communications in a cell will require better tools for microchemical quantitation and identification. We sought to assemble and optimize a microfluidics-based instrument for automation of serial chemical and enzymatic reactions on the smallest possible scale, while maintaining the capacity to analyze a large portion of the end-products. Here we describe a miniaturized, fully integrated and automated system, consisting of multiple rotary valves, reaction and collector modules, all connected by capillary lines, that can deliver about 70% of the end-products, in a 5-μL volume, to any analytical device with low flow-injection or -infusion (e.g. cLC or NanoESI-MS). A near total control of flow path combinations and directions, temperatures and gas pressures enables precise execution of complex biochemical laboratory procedures. Instrument performance was clearly demonstrated by partially sequencing 100 femtomoles of an intact protein using classical Edman chemistry in combination with capillary-bore liquid chromatographic identification. To our knowledge, this is the smallest amount of protein ever reported to be successfully analyzed in this way. Near quantitative transfer of reaction end-products from a pressurized micro-vial, in a minimal volume and at exceedingly low flows, could male any biochemical process fully compatible with NanoESI MS or MS/MS analysis;[31,32] for instance, protein digestion in combination with chemical modification(s).

REFERENCES (INDICATED BY SUPERSCRIPT)

(1) Ramsey, J. M. *Nat. Biotechnol.* 1999, 17, 1061–1062.

(2) Xue, Q.; Dunayevskiy, Y. M.; Foret, F.; Karger, B. L. *Rapid Commun. Mass Spectrom.* 1997, 11, 1253–1256.

(3) Figeys, D.; Aebersold, R. *Anal. Chem.* 1998, 70, 3721–3727.

(4) Khandurina, J.; McKnight, T. E.; Jacobson, S. C.; Waters, L. C.; Foote, R. S.; Ramsey. J. M. *Anal Chem.* 2000, 72, 2995–3000.

(5) Mann, M. *Trends Bioch. Sci.* 1996, 21, 494–495.

(6) Roepsdorff, P. *Curr. Biol.* 1997, 8, 6–13.

(7) Yates III, J. R. *J. Mass Spectrom.* 1998, 33, 1–19.

(8) Haynes, P. A.; Gygi, S. P.; Figeys, D.; Aebersold, R. *Electrophoresis* 1998, 19, 1862–1871.

(9) Edman, P. *Acta Chem. Scand.* 1950, 4, 277–282.

(10) Edman, P. *Acta Chem. Scand.* 1950, 4, 283–293.

(11) Edman, P.; Begg, G. *Eur. J Biochem.* 1967, 1, 80–91.

(12) Laursen, R. A. *Eur. J. Biochem.* 1971, 20, 89–102.

(13) Wittmann-Liebold, B.; Graffunder, H.; Kohls, H. *Anal. Biochem.* 1976, 75, 621–633.

(14) Hunkapiller, M. W.; Hood, L. *Biochemistry* 1978, 17, 2124–2133.

(15) Hewick, R. M.; Hunkapiller, M. W.; Hood, L. E.; Dreyer, W. J. *J. Biol. Chem.* 1981, 256, 7990–7997.

(16) Tempst, P.; Riviere, L. *Anal. Biochemn.* 1989, 183, 290–300.

(17) Tempst, P.; Geromanos, S.; Elicone, C.; Erdjument-Bromage, H. *Medthods* 1994, 6, 248–261.

(18) Totty, N. F., Waterfield, M. D.; Hsuan, J. J. *Protein Sci.* 1992, 1, 1215–1224.

(19) Applied Biosystems Product Note 347607-001. 1996, Procise cLC provides high sensitivity sequence detection.

(20) Simpson, R. J., Moritz, R. L., Begg, G. S., Rubira, M. R.; Nice, E. C. *Anal. Biochem.* 1989,177, 221–236.

(21) Davis, M. T.; Lee, T. D. *Protein Sci.* 1992, 1, 935–944.

(22) Elicone, C.; Lui, M.; Geromanos, S.; Erdjument-Bromage, H.; Tempst. P. *J. Chromatogr.* 1994, 676, 121–137.

(23) Wong, S. W.; Grimley, C.; Padua, J. H.; Bourell, J. H.; Henzel, W. J. In: *Techniques in Protein Chemistry IV* (Hogue-Angeletti, R., Ed.) 1993, Academic Press, San Diego, Calif. pp.371–378.

(24) Erdjument-Bromage, H.; Lui, M.; Sabatini, D. M.; Snyder, S. H.; Tempst, P. *Protein Sci.* 1994, 3, 2435–2446.

(25) Blacher, R. W. and Wieser, J. H. In: *Techniques in Protein Chemistry IV* (Hogue-Angeletti, R., Ed.) 1993, Academic Press, San Diego, Calif. pp.427–433

(26) Moritz, R. L.; Simpson, R. J. *J. Chromatogr.* 1992, 599, 119–130.

(27) Cheng, Y.-F.; Dovichi, N. J. *Science* 1988, 242, 562–564.

(28) Wu, S.; Dovichi, N. J. *Talanta* 1992, 39, 173–178.

(29) Aebersold, R.; Bures, E. J.; Namchuk, M.; Goghari, M. H.; Shushan, B.; Covey, T. C. *Protein Sci.* 1992, 1, 494–503.

(30) Bailey, J. M.; Tu, O.; Basic, C.; Issai, G; Shively, J. E. In: *Techniques in Protein Chemistry IV* (Hogue-Angeletti, R., Ed.) 1994, Academic Press, San Diego, Calif. pp.169–178.

(31) Geromanos, S.; Freckleton, G.; Tempst, P. *Anal. Chem.* 2000, 72, 777–790.

(32) Wilm, M. S.; Mann. M. *Anal. Chem.* 1996, 68, 1–8.

(33) Ambler, R. P. *Biochem. J.* 1963, 89, 349–377.

(34) Tarr, G.; Beecher, J. F.; Bell, M.; McKean, D. J. *Anal. Biochemn.* 1978, 84, 622–627.

Table 1. Comparison of automated protein sequencing instruments: Applied Biosystems 'cLC494' and 'PSMSK'.

RXN, reaction; CNV, conversion; Evalve, cartridge reagent/solvent block or valve; other abbreviations, see key in FIG. 1 or Glossary. R1 corresponds to 11 in FIG. 1C, R3 to 13, R4 to 14, S1 to 144d, S123 to each of 144a, 144b, and 144c.

"Flask" in the table refers to the conversion vessel 101.

Tables 2A and 2B. Model 'PSMSK' reaction and conversion cycles.

RXN, reaction; CNV, conversion; NLE-Std, PTH-norleucine (30 fmol/µL acetonitrile); reaction temperature, 48iC; conversion temperature, 64iC. Total reaction cycle time, ~68 min; total conversion cycle time, ~45 min; further details, see FIG. 1 and elsewhere in the application.

Table 3. Brief history of Edman protein sequencing.

TABLE 1

A. Wetted Surfaces:

| System | RXN Disc | | | RXN Block |
|---|---|---|---|---|
| | Diameter mm | Surface mm² | Volume µL | Cavity Volume µL |
| cLC494 | 6 | 28 | 8 | 32 |
| PSMSK | 3 | 7 | 2 | 4 |

| System | Flow Path Volume | | | Injector |
|---|---|---|---|---|
| | Evalve-Flask µL | Flask-Injector µL | Total µL | Loop Volume µL |
| cLC494 | 248 | 130 | 378 | 50 |
| PSMSK | 11 | 1.5 | 12.5 | 5 |

B. Reagents/Solvents Delivery:

| System | Disc mm | Polybrene mg | RXN | | WASH (S123) | |
|---|---|---|---|---|---|---|
| | | | R1 µL | R3 µL | Volume µL | Vol./Area µL/mm² |
| cLC494 | 6 | 0.75 | 8 | 32 | 920 | 33 |
| PSMSK | 3 | 0.18 | 2 | 4 | 270 | 39 |

| System | ATZ Transfer | | CNV | | | Injection Percentage % |
|---|---|---|---|---|---|---|
| | Volume µL | Vol./Area µL/mm² | S4(preATZ) µL | R4 µL | S4(PTH) µL | |
| cLC494 | 291 | 10.4 | 60 | 10 | 91 | 55 |
| PSMSK | 76 | 10.9 | 7.5 | 7.5 | 7.5 | 67 |

TABLE 2A

Reaction Cycle - #27 Glass Fiber

| | | Time Elapsed (sec) | |
|---|---|---|---|
| Step | Description | Core | Step |
| 1 | Deliver TMA to Cartridge | 20 | 68 |
| 2 | Deliver PITC to Cartridge | 10 | 35 |
| 3 | Pause | 20 | 20 |
| 4 | Deliver TMA to Cartridge | 400 | 448 |
| 5 | Deliver PITC to Cartridge | 10 | 35 |
| 6 | Pause | 20 | 20 |
| 7 | Deliver TMA to Cartridge | 400 | 448 |
| 8 | Deliver PITC to Cartridge | 10 | 35 |
| 9 | Pause | 20 | 20 |
| 10 | Deliver TMA to Cartridge | 400 | 488 |
| 11 | AR4 to Cartridge | 240 | 248 |
| 12 | Deliver Heptane to Cartridge | 60 | 83 |
| 13 | Pause | 10 | 10 |
| 14 | AR4 to Cartridge | 10 | 18 |
| 15 | Deliver Heptane to Cartridge | 60 | 83 |
| 16 | Pause | 10 | 10 |
| 17 | AR4 to Cartridge | 10 | 18 |
| 18 | Deliver BuCl to Cartridge | 60 | 83 |
| 19 | Pause | 10 | 10 |
| 20 | AR4 to Cartridge | 10 | 18 |
| 21 | Deliver EtAc to Cartridge | 60 | 83 |
| 22 | Pause | 10 | 10 |
| 23 | AR4 to Cartridge | 10 | 18 |
| 24 | Deliver EtAc to Cartridge | 60 | 83 |
| 25 | Pause | 10 | 10 |
| 26 | AR4 to Cartridge | 10 | 18 |
| 27 | Deliver EtAc to Cartridge | 60 | 83 |
| 28 | Pause | 10 | 10 |
| 29 | AR4 to Cartridge | 150 | 158 |
| 30 | Deliver Liquid TFA to Cartridge | 10 | 104 |
| 31 | Load RXN Loop with EtAc | 15 | 23 |
| 32 | Clear RXN Loop to Waste with AR5 | 10 | 10 |
| 33 | Load RXN Loop with EtAc | 15 | 23 |
| 34 | Clear RXN Loop to Waste with AR5 | 40 | 40 |
| 35 | AR4 to Cartridge | 20 | 248 |
| 36 | Prep Transfer | 10 | 10 |
| 37 | Deliver Heptane to Midpoint | 12 | 32 |
| 38 | Transfer Pause | 15 | 15 |
| 39 | Transfer with BuCl Part 1 | 15 | 15 |
| 40 | Transfer Pause | 15 | 15 |
| 41 | Transfer with AR4 | 45 | 55 |
| 42 | Transfer Argon Pulse | 40 | 40 |
| 43 | Transfer with BuCl Part 1 | 15 | 15 |
| 44 | Transfer Pause | 10 | 10 |
| 45 | Transfer with AR4 | 30 | 40 |
| 46 | Transfer Argon Pulse | 30 | 30 |
| 47 | Transfer with BuCl Part 1 | 15 | 15 |
| 48 | Transfer Pause | 10 | 10 |
| 49 | Transfer with AR4 | 30 | 40 |
| 50 | Transfer Argon Pulse | 30 | 30 |
| 51 | Transfer with BuCl Part 1 | 15 | 15 |
| 52 | Transfer Pause | 10 | 10 |
| 53 | Transfer with AR4 | 30 | 40 |
| 54 | Transfer Argon Pulse | 30 | 30 |
| 55 | End Transfer | 1 | 1 |
| 56 | Deliver BuCl to Cartridge | 30 | 53 |
| 57 | AR4 to Cartridge | 120 | 128 |
| 58 | Load RXN loop with BuCl | 60 | 68 |
| 59 | Load RXN loop with Heptane | 60 | 68 |
| 60 | Load RXN loop with EtAc | 60 | 68 |
| 61 | AR4 to Cartridge | 120 | 128 |

TABLE 2B

Conversion Cycle - #28 Low Pressure Conversion

| | | Time Elapsed (sec) | |
|---|---|---|---|
| Step | Description | Core | Step |
| 1 | Empty Flask to Injector | 60 | 68 |
| 2 | Rinse Vent/Flask with 25% TFA | 45 | 72 |
| 3 | Rinse Vent/Flask with 25% TFA | 45 | 72 |
| 4 | Dry Flask with AR6 | 60 | 68 |
| 5 | Empty Flask to Waste with AR6 | 400 | 408 |
| 6 | Rinse Vent/Flask with 10% MeCN | 30 | 52 |
| 7 | Rinse Vent/Flask with 10% MeCN | 30 | 52 |
| 8 | Dry Flask with AR6 | 60 | 68 |
| 9 | Empty Flask to Waste with AR6 | 300 | 308 |
| 10 | Dry Flask with AR5 | 60 | 68 |
| 11 | Load CNV Loop with NLE-Std | 10 | 16 |
| 12 | Deliver CNV Loop to Flask with AR5 | 80 | 80 |
| 13 | Load CNV Loop with 25% TFA | 15 | 21 |
| 14 | Deliver CNV Loop to Flask with AR5 | 20 | 20 |
| 15 | Ready to Receive | 1 | 1 |
| 16 | Deliver CNV Loop to Flask with AR4 | 1000 | 1000 |
| 17 | Load Injector Loop with AR5 | 240 | 248 |
| 18 | Load CNV Loop with 10% MeCN | 10 | 16 |

TABLE 2B-continued

Conversion Cycle - #28 Low Pressure Conversion

| | | Time Elapsed (sec) | |
|---|---|---|---|
| Step | Description | Core | Step |
| 19 | Deliver CNV Loop to Flask with AR5 | 20 | 20 |
| 20 | Pause | 10 | 10 |
| 21 | Deliver CNV Loop to Flask with AR5 | 20 | 20 |
| 22 | Pause | 10 | 10 |
| 23 | Load Injector Loop with AR5 | 15 | 23 |
| 24 | Relay 1 On: Start HPLC | 2 | 2 |
| 25 | Relay 1 Off | 2 | 2 |

TABLE 3

Brief History of Edman Protein Sequencing

| YEAR | | SCALE | REFERENCES |
|---|---|---|---|
| 1950 | Edman Chemistry | 1 mmol | 9,10 |
| 1955–56 | Practical Manual Sequencing | 1 mmol | 33 |
| 1967 | Spinning-Cup Sequencer | 200 nmol | 11 |
| 1968–77 | Various Improvements | 10–100 nmol | 13,34 |
| 1978 | Picomole HPLC analysis | 0.5–5 nmol | 14 |
| 1981 | Gas-Phase Sequencer | 20–100 pmol | 15 |
| 1986 | 'On-line' HPLC | 5–10 pmol | |
| 1987–94 | Various Optimizations | 2–5 pmol | 16,17,18 |
| 1996 | Applied Biosystems cLC | 1 pmol | 19 |
| 2000 | Microfluidics (PSMSK) | 100–200 fmol | this patent application |

What is claimed is:

1. A system for carrying out one or more chemical reactions, said system comprising a rotary selector valve and a rotary switching valve, each valve under the control of a computer, the internal volumes of the selector and switching valves each being 1.5 μl or less wherein the rotary selector valve comprises, in a first unit, a central common port and a circular array of a plurality of peripheral ports such that the main axis of the common port is the same as is the main axis through the circular array, and wherein said valve comprises, on a second unit, a radial connector channel, the first and second units being juxtaposed such that there is a single continuous selector channel formed by the common port, the connector channel, and a peripheral port, the selection of the peripheral port under control of the computer, the internal volume of the continuous selector channel being the internal volume of the valve, and wherein the rotary switching valve comprises a circular array of three or more peripheral ports in a first unit and a connector channel in a second unit, the two units being juxtaposed such that there is a continuous switching channel formed by a first peripheral port, the connector channel, and a second peripheral port, the selection of two peripheral ports being under the control of the computer, the internal volume of the continuous switching channel being the internal volume of the valve.

2. A system of claim 1 wherein the rotary selector valve is connected by its central common port to a first peripheral port of the rotary switching valve, the connection being accomplished by a conduit means having an internal volume between 0.5 μL and 10 μL.

3. A system of claim 2 wherein the total internal volume of the selector and switching valves are each in the range 0.04 μL to 1.5 μL.

4. A system of claim 3 wherein the total internal volume of the selector and switching valves are in the range 0.1 μL to 0.5 μL.

5. A system of claim 2, said system further comprising:

a reaction vessel connected to the second peripheral port in the continuous switching channel of the switching valve, a first and second reagent vessel, said vessels each connected to first and second peripheral ports of the selector valve, said vessels each connected to a gas source comprising a gas under pressure.

6. A system of claim 5, the selector valve thereof being a first selector valve and the switching valve thereof being a first switching valve, said system further comprising:

a second rotary selector valve connected to a second rotary switching valve;

a third rotary switching valve;

a conversion vessel connected to receive output from said third rotary switching valve, a restraining means for restraining unprocessed polymer in the reaction vessel;

third and fourth reagent vessels connected to provide fluid to said conversion vessel;

wherein said second rotary valve, second switching valve, and third switching valve are each under the control of the computer and each have an internal volume of 1.5 μl or less.

7. A reaction process under the control of a computer said process comprising the steps of:

1) Delivering, from a reagent vessel under pressure from a gas source, a volume of a reagent via a delivery line to a reaction vessel wherein the total volume delivered for purposes of a reaction in the reaction vessel is in the range 0.5 uL to 10 uL, and wherein flow through the delivery line is under the control of a computer-controlled rotary switching valve connected to a rotary selector valve;

2) Washing said valves and delivery line with a wash-solvent:

3) Repeating step (1) optionally with a reagent, reagent vessel and/or gas source different from that used in step (1)

4) Placing a polymer in a reaction vessel, said polymer restrained in said vessel;

5) Delivering to said reaction vessel, from a first reagent vessel under pressure from a gas source, a volume of a first fluid, said fluid comprising a first reagent, which reagent will bind to a terminal monomer on the polymer;

6) Delivering to said reaction vessel, from a second reagent vessel under pressure from a gas source, a volume of a second fluid, which fluid will cause a terminal monomer-reagent moiety to be cleaved from the polymer;

7) causing all or part of the fluid in the reaction flask to be transferred under gas pressure via a delivery line to a conversion flask while allowing the polymer, less the terminal monomer, to remain in the reaction vessel;

8) Prior or after step (7), delivering from a third reagent vessel under pressure from a gas source a volume of a third fluid such that the combination of said fluid and the fluid transferred in step (7) to the reaction flask will cause the terminal monomer-reagent moiety to be cleaved to create a terminal monomer free of covalently bound reagent;

(9) Transferring under gas pressure from a gas source said terminal monomer created in step (8) to an analytical device that will identify the nature of the terminal monomer;

wherein each volume delivered in steps (5), (6), (7), (8), is in the range 0.2 uL to 10 uL, and the volume delivered in step (9) is in the range 1 uL to 10 uL.

8. A process of claim 7 wherein steps (4)–(9) are performed a plurality of times.

9. A process of claim 7, wherein the process comprises sequentially delivering acid, organic solvent, and base to the reaction vessel.

10. A process of claim 7 wherein the reaction vessel is kept free of air and oxygen.

11. A process of claim 7 wherein the reaction vessel and the conversion vessel are kept free of air and oxygen.

* * * * *